(12) United States Patent
Verfaillie et al.

(10) Patent No.: US 8,252,280 B1
(45) Date of Patent: *Aug. 28, 2012

(54) MAPC GENERATION OF MUSCLE

(75) Inventors: Catherine M. Verfaillie, St. Paul, MN (US); Robert Gallegos, Apple Valley, MN (US); Michael Jerosch-Herold, Portland, OR (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/105,372

(22) Filed: May 11, 2011

Related U.S. Application Data

(63) Continuation of application No. 10/945,528, filed on Sep. 20, 2004, now abandoned, which is a continuation-in-part of application No. 10/048,757, filed as application No. PCT/US00/21387 on Aug. 4, 2000, now Pat. No. 7,015,037, which is a continuation-in-part of application No. 12/907,495, filed on Oct. 19, 2010, which is a continuation of application No. 10/467,963, filed as application No. PCT/US02/04652 on Feb. 14, 2002, now Pat. No. 7,838,289.

(60) Provisional application No. 60/147,324, filed on Aug. 5, 1999, provisional application No. 60/164,650, filed on Nov. 10, 1999, provisional application No. 60/504,125, filed on Sep. 19, 2003, provisional application No. 60/343,836, filed on Oct. 25, 2001, provisional application No. 60/310,625, filed on Aug. 7, 2001, provisional application No. 60/269,062, filed on Feb. 15, 2001, provisional application No. 60/268,786, filed on Feb. 14, 2001.

(51) Int. Cl.
*A61K 35/12* (2006.01)
(52) U.S. Cl. ........ 424/93.7; 424/577; 435/366; 435/325
(58) Field of Classification Search ............... 424/93.7, 424/577; 435/366, 325
See application file for complete search history.

(56) References Cited

U.S. PATENT DOCUMENTS

| | | | |
|---|---|---|---|
| 4,714,680 A | 12/1987 | Civin | |
| 4,965,204 A | 10/1990 | Civin | |
| 5,035,994 A | 7/1991 | Civin | |
| 5,061,620 A | 10/1991 | Tsukamoto et al. | |
| 5,130,144 A | 7/1992 | Civin | |
| 5,486,359 A | 1/1996 | Caplan et al. | |
| 5,589,376 A | 12/1996 | Anderson et al. | |
| 5,602,301 A | 2/1997 | Field | |
| 5,635,386 A | 6/1997 | Palsson et al. | |
| 5,648,248 A | 7/1997 | Zenke et al. | |
| 5,654,183 A | 8/1997 | Anderson et al. | |
| 5,672,499 A | 9/1997 | Anderson et al. | |
| 5,733,727 A | 3/1998 | Field | |
| 5,827,735 A | 10/1998 | Young et al. | |
| 5,843,780 A | 12/1998 | Thomson | |
| 5,906,934 A | 5/1999 | Grande et al. | |
| 5,928,943 A | 7/1999 | Franz et al. | |
| 6,015,671 A | 1/2000 | Field | |
| 6,090,622 A | 7/2000 | Gearhart et al. | |
| 6,090,625 A | 7/2000 | Abuljadayel | |
| 6,146,888 A | 11/2000 | Smith et al. | |
| 6,200,806 B1 | 3/2001 | Thomson | |
| 6,214,369 B1 | 4/2001 | Grande et al. | |
| 6,271,436 B1 | 8/2001 | Piedrahita et al. | |
| 6,280,718 B1 | 8/2001 | Kaufman et al. | |
| 6,306,575 B1 | 10/2001 | Thomas et al. | |
| 6,361,997 B1 | 3/2002 | Huss | |
| 6,387,369 B1 | 5/2002 | Pittenger et al. | |
| 6,653,134 B2 | 11/2003 | Prockop et al. | |
| 6,777,231 B1 | 8/2004 | Katz et al. | |
| 7,056,738 B2 | 6/2006 | Prockop et al. | |
| 7,229,827 B2 | 6/2007 | Kim et al. | |
| 7,514,074 B2 | 4/2009 | Pittenger et al. | |
| 2001/0005591 A1 | 6/2001 | Qasba et al. | |
| 2001/0012513 A1 | 8/2001 | Robl et al. | |
| 2001/0024824 A1 | 9/2001 | Moss et al. | |
| 2001/0024825 A1 | 9/2001 | Thomson | |
| 2001/0033834 A1 | 10/2001 | Wilkison et al. | |
| 2001/0046489 A1 | 11/2001 | Habener et al. | |
| 2002/0061587 A1 | 5/2002 | Anversa | |
| 2002/0098167 A1 | 7/2002 | Anversa et al. | |
| 2002/0164794 A1 | 11/2002 | Wernet | |
| 2003/0003090 A1 | 1/2003 | Prockop et al. | |
| 2003/0054973 A1 | 3/2003 | Anversa | |
| 2003/0059414 A1 | 3/2003 | Ho et al. | |
| 2004/0107453 A1 | 6/2004 | Furcht et al. | |
| 2004/0235165 A1 | 11/2004 | Prockop et al. | |
| 2005/0169896 A1 | 8/2005 | Li et al. | |
| 2005/0283844 A1 | 12/2005 | Furcht et al. | |
| 2006/0008450 A1 | 1/2006 | Verfaillie et al. | |
| 2006/0263337 A1 | 11/2006 | Maziarz et al. | |
| 2007/0003530 A1 | 1/2007 | Pittenger et al. | |

FOREIGN PATENT DOCUMENTS

CA 2191655 6/1997

(Continued)

OTHER PUBLICATIONS

Giles, J., "The trouble with replication" Nature, 422:344-347 (2006).
Verfaillie, C.M., "Multipotent adult progenitor cells: an update" Novartis Symp., 254:55-65 (2005).

(Continued)

*Primary Examiner* — Taeyoon Kim
(74) *Attorney, Agent, or Firm* — Tarolli, Sundheim, Covell & Tummino LLP

(57) ABSTRACT

The present invention relates to methods of increasing function and/or mass in damaged striated muscle tissue of interest (e.g., cardiac or muscle tissue) by providing of a population of multipotent adult progenitor cells ("MAPCs"), which effectively generate new striated muscle over time.

17 Claims, 11 Drawing Sheets

FOREIGN PATENT DOCUMENTS

| | | |
|---|---|---|
| EP | 0627487 A2 | 12/1994 |
| WO | WO-95/03062 A1 | 2/1995 |
| WO | WO-95/10599 A1 | 4/1995 |
| WO | WO-95/14079 A1 | 5/1995 |
| WO | WO-96/16163 A1 | 5/1996 |
| WO | WO-96/23870 A1 | 8/1996 |
| WO | WO-96/28539 A1 | 9/1996 |
| WO | WO-99/11758 A2 | 3/1999 |
| WO | WO-99/15629 A1 | 4/1999 |
| WO | WO-99/16863 A1 | 4/1999 |
| WO | WO-99/27076 A1 | 6/1999 |
| WO | WO-99/35243 A2 | 7/1999 |
| WO | WO-99/53021 A1 | 10/1999 |
| WO | WO-00/12682 A1 | 3/2000 |
| WO | WO-00/32140 A1 | 6/2000 |
| WO | WO-01/04268 A1 | 1/2001 |
| WO | WO-01/05944 A1 | 1/2001 |
| WO | WO-01/08691 A1 | 2/2001 |
| WO | WO-01/11011 A2 | 2/2001 |
| WO | WO-01/21766 A2 | 3/2001 |
| WO | WO-01/21767 A2 | 3/2001 |
| WO | WO-01/23528 A1 | 4/2001 |
| WO | WO-01/29206 A1 | 4/2001 |
| WO | WO-01/34776 A1 | 5/2001 |
| WO | WO-01/39784 A1 | 6/2001 |
| WO | WO-01/53461 A1 | 7/2001 |
| WO | WO-0151610 A1 | 7/2001 |
| WO | WO-01/62899 A2 | 8/2001 |
| WO | WO-01/62901 A2 | 8/2001 |
| WO | WO-01/66697 A2 | 9/2001 |
| WO | WO-01/68815 A1 | 9/2001 |
| WO | WO-02/08388 A2 | 1/2002 |
| WO | WO-02/34890 A2 | 5/2002 |
| WO | WO-02/064748 A2 | 8/2002 |

OTHER PUBLICATIONS

Young et al., "Human reserve pluripotent mesenchymal stem cells are present in the connective tissues of skeletal muscle and dermis derived from fetal, adult, and geriatric donors" The Anatomical Record; 264:51-62 (2001).

Nagaya et al., "Intravenous administration of mesenchymal stem cells improves cardiac function in rats with actue myocardial infarction through angiogenesis and myogenesis" Am. J. Physiol. Heart Circ. Phyiol.; 287: H2670-H2676 (2004).

Freyman et al., "A quantitative, randomized study evaluating three methods of mesenchymal stem cell delivery following myocardial infarction" European Heart Journal; 27:1114-1122 (2006).

Dai et al., "Allogeneic mesenchymal stem cell transplantation in postinfarcted rat myocardium. Short- and long-term effects" Circulation; 112:214-223 (2005).

Kim et al., "Cell transplantation improves ventricular function after a myocardial infarction: a preclinical study of human unrestricted somatic stem cells in a porcine model" Circulation; 112:I96-I104 (2005).

Amado et al., "Cardiac repair with intramyocardial injection of allogeneic mesenchymal stem cells after myocardial infarction" PNAS; 102:11474-11479 (2005).

Pelacho et al., "Multipotent adult progenitor cell transplantation increases vascularity and improves left ventricular function after myocardial infarction" J. Tissue Eng. Regen. Med; 1:51-59 (2007).

Second Supplemental Information Disclosure Statement filed in U.S. Appl. No. 11/151,689 on Dec. 24, 2008 (with attachment).

"Adult Marrow Cells Show Versatility", *Associated Press, The New York Times*, (Jan. 25, 2002), 2 pgs.

"Cambrex Specimens, Poietics® Human Mesenchymal Stem Cell Systems", Cambrex BioScience, Walkersville, Inc., (2005).

Alfonso, Z., et al., "Osteoblast Precursor Cells Are Found in the Low-Density Fraction of Umbilical Cord Blood", *Blood*, 94(10)(Suppl. 1, Part 2), (Abstract #3897), (Nov. 15, 1999), p. 161b.

Amit, M., et al., "Clonally Derived Human Embryonic Stem Cell Lines Maintain Pluripotency and Proliferative Potential for Prolonged Periods of Culture", *Developmental Biology*, 227(2), (2000),271-278.

Asahara, T., "Isolation of Putative Progenitor Endothelial Cells for Angiogenesis", *Science*, 275(5302), (Feb. 14, 1997),964-967.

Asahara, T., et al., "Stem Cell Therapy and Gene Transfer for Regeneration", *Gene Therapy*, 7(6), (2000),451-457.

Beltrami, A. P., et al., "Evidence That Human Cardiac Myocytes Divide After Myocardial Infarction", *The New England Journal of Medicine*, 344(23), (Jun. 7,2001),1750-1757.

Ben-Shushan, E., et al., "Rex-1, a Gene Encoding a Transcription Factor Expressed in the Early Embryo, is Regulated via Oct-3/4 and Oct-6 Binding to an Octamer Site and a Novel Protein, Rox-1, Binding to an Adjacent Site", *Molecular & Cellular Biology*, 18(4),(Apr. 1998),1866-1878.

Bianco, P., et al., "Stem Cells in Tissue Engineering", *Nature*, 414, (Nov. 1, 2001),118-121.

Bjornson, C. R., et al., "Turning Brain Into Blood: A Hematopoietic Fate Adopted by Adult Neural Stem Cells in vivo", *Science*, 283(5401), (Jan. 22, 1999), 534-537.

Bongso, A., et al., "Isolation and Culture of Inner Cell Mass Cells From Human Blastocysts", *Human Reproduction*, 9(11), (1994), 2110-2117.

Bongso, A., et al., "The Growth of Inner Cell Mass Cells From Human Blastocysts", *Theriogenology*, 41, (1994),p. 167.

Bouwens, L., "Transdifferentiation Versus Stem Cell Hypothesis for the Regeneration of Islet Beta-Cells in the Pancreas", *Microscopy Research and Technique*, 43(4), (1998),332-336.

Bruni, C., "Mitotic Activity of Muscle Satellite Cells During the Early Stages of Rhabdomyosarcomas Induction With Nickel Subsulfide", *In: Muscle Regeneration*, Mauro, A., et al., Editors, Raven Press, New York, NY,(1979),265-273.

Brüstle, O., et al., "Embryonic Stem Cell-Derived Glial Precursors: A Source of Myelinating Transplants", *Science*, 285(5428), (Jul. 30, 1999),754-756.

Campion, D. R., "The Muscle Satellite Cell: A Review", *International Review of Cytology*, 87, (1984),225-251.

Cargill, M., et al., "Characterization of Single-Nucleotide Polymorphisms in Coding Regions of Genes", *Nature Genetics*, 22, (Jul. 1999),231-238.

Cassiede, P., et al., "Osteochondrogenic Potential of Marrow Mesenchymal Progenitor Cells Exposed to TGF-β1 or PDGF-BB as Assay invivo and in vitro", *Journal of Bone and Mineral Research.*, 11 (9), (1996),1264-1273.

Chalmers-Redman, R. M., et al., "In Vitro Propagation and Inducible Differentiation of Multipotential Progenitor Cells From Human Fetal Brain", *Neuroscience*, 76(4), (1997),1121-1128.

Chen, J., et al., "Therapeutic Benefit of Intravenous Administration of Bone Marrow Stromal Cells After Cerebral Ischemia in Rats", *Stroke*, 32(4), (2001),1005-1011.

Cutler, C., et al., "Peripheral Blood Stem Cells for Allogeneic Transplantation: A Review", *Stem Cells*, 19, (2001),108-117.

Dewitt, N., *Nature insight—Stem Cells*, vol. 414, No. 6859, (2001),87-131.

Doetschman, T., et al., "Establishment of Hamster Blastocyst-Derived Embryonic Stem (ES) Cells", *Developmental Biology*, 127(1), (1998),224-227.

Donovan, P. J., et al., "The End of the Beginning for Pluripotent Stem Cells", *Nature*, 414, (Nov. 1, 2001),92-97.

Erices, A., et al., "Mesenchymal Progenitor Cells in Human Umbilical Cord Blood", *British Journal of Haematology*, 109, (2000),235-242.

Etzion, S., et al., "Influence of Embryonic Cardiomyocyte Transplantation on the Progression of Heart Failure in a Rat Model of Extensive Myocardial Infarction", *J. Mol. Cell. Cardiol.*, 33(7), (2001)1321-1330.

Evans, M. J., et al., "Establishment in Culture of Pluripotential Cells From Mouse Embryos", *Nature*, 292(5819), (Jul. 9, 1981),154-156.

First, N. L., et al., "Systems for Production of Calves From Cultured Bovine Embryonic Cells", *Reproduction, Fertility and Development*, 6(5), (1994),553-562.

Galli, C., et al., "Embryonic Stem Cells in Farm Animals", *Zygote*, 2(4), (1994),385-389.

Game, D. S., et al., "Rejection Mechanisms in Transplantation", *Wien Klin Wochenschr*, vol. 113/20-21, (2001),832-838.

Geiger, H., et al., "Globin Gene Expression is Reprogrammed in Chimeras Generated by Injecting Adult Hematopoietic Stern Cells Into Mouse Blastocysts", *Cell*, 93(6), (Jun. 12, 1998),1055-1065.

Geissler, E. K., et al., "Effective Use of Donor MHC Class I Gene Therapy in Organ Transplantation: Prevention of Antibody-Mediated Hyperacute Heart Allograft Rejection in Highly Sensitized Rat Recipients", *Human Gene Therapy*, 11(3), (2000), 459-469.

Gmyr, V., et al., "Adult Human Cytokeratin 19-Positive Cells Reexpress Insulin Promoter Factor I In Vitro—Further Evidence for Pluripotent Pancreatic Stem Cells in Humans", *Diabetes*, 49(10), (2000),1671-1680.

Goodwin, H. S., et al., "Multilineage Differentiation Activity by Cells Isolated From Umbilical Cord Blood: Expression of Bone, Fat, and Neural Markers", *Biology of Blood and Marrow Transplantation*, 7, (2001),581-588.

Graves, K. H., et al., "Derivation and Characterization of Putative Pluripotential Embryonic Stem Cells From Preimplantation Rabbit Embryos", *Molecular Reproduction and Development*, 36(4), (1993),424-433.

Grigoriadou, K., et al., "MHC Class la Molecules Alone Control NK-Mediated Bone Marrow Graft Rejection", *European Journal of Immunology*, 29(11), (Nov. 1999),3683-3690.

Gulcher, J., et al., "Population Genetics: Laying the Groundwork for Genetic Disease Modeling and Targeting", *Clinical Chemical Laboratory Medicine*, 36(8), (1998),523-727.

Gunsilius, E., et al, "Hematopoietic Stem Cells", *Biomedicine & Pharmacotherapy*, 55(4), (2001), 186-194.

Gupta, P., "Human Bone Marrow Derived Mesodermal Progenitor Cells (MPC) In Vitro Correct the Biochemical Abnormality in Hurler Syndrome", *Abstract No. 1199, American Society for Hematology*, (Dec. 2001),1 pg.

Gussoni, E., et al., "Long-Term Persistence of Donor Nuclei in Duchenne Muscular Dystrophy Patient Receiving Bone Marrow Transplantation", *The Journal of Clinical Investigation*, 110(6), (Sep. 2002),807-814.

Hamilton, D. P., "The Tissue Bank's Shaky Underpinnings", *Science*, 257(5072), (Aug. 14, 1992), p. 869.

Handyside, A., et al., "Towards the Isolation of Embryonal Stem Cell Lines From the Sheep", *Development Genes and Evolution*, 196(3), (1957),185-190.

Handyside, A. H., et al., "Use of BRL-Conditioned Medium in Combination With Feeder Layers to Isolate a Diploid Embryonal Stem Cell Line", *Development Genes and Evolution*, 198(1), (1989)48-56.

Hilton, D. J., et al., "Distribution and Comparison of Receptors for Leukemia Inhibitory Factor on Murine Hemopoietic and Hepatic Cells", *Journal of Cellular Physiology*, 146(2), (1991),207-215.

Hughes, S., "Cardiac Stem Cells", *Journal of Pathology*, 197(4), (2002),468-478.

Huilin, Q., et al., "Identification of Genes Responsible for Bone Differentiation from Human Bone Marrow Derived Multipotent Adult Stem Cells (MASC)", *Blood*, 96(11)(Part 1), (Nov. 16, 2000), (Nov. 16, 2000), 70a-71a.

Iannaccone, P. M., et al., "Pluripotent Embryonic Stem Cells From the Rat are Capable of Producing Chimeras", *Developmental Biology*, 163(1), (1994),288-292.

Itskovitz-Eldor, J., et al., "Differentiation of Human Embryonic Stem Cells Into Embryoid Bodies Compromising the Three Embryonic Germ Layers", *Molecular Medicine*, 6(2), (2000),88-95.

Jiang, Y., et al., "Multipotent Progenitor Cells can be Isolated From Postnatal Murine Bone Marrow, Muscle, and Brain", *Experimental Hematology*, 30(8), (Aug. 2002),896-904.

Jiang, Y., et al., "Pluripotency of Mesenchymal Stem Cells Derived From Adult Marrow", *Nature*, 418(6893), (Jul. 4, 2002),41-49.

Jiao, S., et al., "Long-Term Correction of Rat Model of Parkinson's Disease by Gene Therapy", *Nature*, 362, (Apr. 1, 1993),450-453.

Jones, J. M., et al., "Human Embryonic Stem Cell Technology", *Seminars in Reproductive Medicine*, 18(2), (2000),219-223.

Keene, C. D., et al., "Phenotypic Expression of Transplanted Human Bone Marrow-Derived Multipotent Adult Stem Cell Into the Rat CNS", *Experimental Neurology*, 164(2), (Abstract Only), Seventh Annual Conference of the American Society for Neural Transplantation and Repair (Clearwater, FL, Apr. 27-30, 2000),(Aug. 2000),p. 465.

Kehat, I., et al., "Human Embryonic Stem Cells can Differentiate Into Myocytes With Structural and Functional Properties of Cardiomyocytes", *The Journal of Clinical Investigation*, 108(3), (Aug. 2001),407-414.

Kelly, L. D., et al., "DNA Microarray Analysis of Genes Regulated During the Differentiation of Embryonic Stem Cells", *Molecular Reproduction and Development*, 56(2), (2000),113-123.

Kessler, P. D., et al., "Myoblast Cell Graffing Into Heart Muscle: Cellular Biology and Potential Applications", *Annual Review of Physiology*, 61, (1999),219-242.

Klug, M. G., et al., "Genetically Selected Cardiomyocytes From Differentiating Embryonic Stem Cells Form Stable Intracardiac Grafts", *The Journal of Clinical Investigation*, 98(1), (1996),216-224.

Kocher, A. A., et at., "Neovascularization of Ischemic Myocardium by Human Bone-Marrow-Derived Angioblasts Prevents Cardiomyocyte Apoptosis, Reduces Remodeling and Improves Cardiac Function", *Nature Medicine*, 7(4), (Apr. 2001),430-436.

Koh, G. Y., et al., "Differentiation and Long-Term Survival of C2C12 Myoblast Grafts in Heart", *The Journal of Clinical investigation*, 92(3), (Sep. 1993),1548-1554.

Koh, G. Y., et al., "Long-Term Survival of AT-1 Cardiomyocyte Grafts in Syngeneic Myocardium", *American Journal of Physiology—Heart and Circulatory Physiology*, (1993),H1727-H1733.

Koh, G. Y., et al., "Strategies for Myocardial Repair", *Journal of Interventional Cardiology*, 8(4), (1995),387-393.

Krause, D. S., et al., "Multi-Organ, Multi-Lineage Engraftment by a Single Bone Marrow-Derived Stem Cell", *Cell*, 105, (May 2001),389-377.

Kuznetsov, S. A., et al., "Factors Required for Bone Marrow Stromal Fibroblast Colony Formation in Vitro", *British Journal of Hematology*, 97(3), (Jun. 1997),561-570.

Lamming, C. E., et al., "Spontaneous Circulation of Myeloid-Lymphoid-Initiating Cells and SCID-Repopulating Cells in Sickle Cell Crisis", *Journal of Clinical Investigation*, 111(6), (Mar. 2003)811-819.

Lennon, D. P., et al., "A Chemically Defined Medium Supports in vitro Proliferation and Maintains the Osteochondral Potential of Rat Marrow-Derived Mesenchymal Stem Cells", *Experimental Cell Research*, 219 (1), (1995),211-222.

Lewis, I. D., et al., "Multi-Lineage Expansion Potential of Primative Hematopoietic Progenitors: Superiority of Umbilical Cord Blood Compared to Mobilized Peripheral Blood", *Experimental Hematology*, 28(9), (2000),1087-1095.

Liu, H., et al., "Myeloid-Lymphoid Initiating Cells (ML-IC) are Highly Enriched in the Rhodamine-c-kit(+)CD33(-)CD38(-) Fracture of Umbilical Cord CD34(+) Cells", *Experimental Hematology*, 30(6), (2002),582-589.

Lodie, T. A., et al., "Systematic Analysis of Reportedly Distinct Populations of Multipotent Bone Marrow-Derived Stem Cells Reveals a Lack of Distinction", *Tissue Engineering*, 8(5), (2002),739-751.

Lovell-Badge, R., "The Future for Stem Cell Research", *Nature*, 414, (Nov. 1, 2001),88-91.

Loweel, S., "Stem Cells Show Their Potential", *Trends in Cell Biology*, 10, (May 2000),210-211.

Marmur, R., et al., "Isolation and Developmental Characterization of Cerebral Cortical Multipotent Progenitors", *Developmental Biology*, 204(2), (1998),577-591.

McLaren, A., "Ethical and Social Considerations of Stem Cell Research", *Nature*, 414, (Nov. 2001),129-131.

Menasche, P., et al., "Myoblast Transplantation for Heart Failure", *The Lancet*, 357(9252), (2001), 279-280.

Menasche, P., "Skeletal Muscle Satellite Cell Transplantation", *Cardiovascular Research*, 58, (2003), 351-357.

Miller, J. S., et al, "Ex Vivo Culture of CD34$^+$/Lin/DR Cells in Stroma-Derived Soluble Factors, Interleukin-3, and Macrophage Inflammatory Protein-1 alpha Maintains Not Only Myeloid But Also Lymphoid Progenitors in a Novel Switch Culture Assay", *Blood*, 91(12), (1998),4516-4522.

Notarianni, E., et al., "Derivation of Pluripotent, Embryonic Cell Lines From the Pig and Sheep", *J. Reprod. Fertil. Suppl.*, 43, (1991),255-260.

Notarianni, E., et al., "Maintenance and Differentiation in Culture of Pluripotential Embryonic Cell Lines From Pig Blastocysts", *J. Reprod. Fertil. Suppl.*, (1990),51-56.

Orlic, D., "Bone Marrow Cells Regenerate infarcted Myocardium", *Nature*, 410(6829), (Apr. 5, 2001),701-705.

Orlic, D., et al., "Transplanted Adult Bone Marrow Cells Repair Myocardial Infarcts in Mice", *Ann. N.Y. Acad. Sci.*, 938, (2001),221-230.

Ott, H. C., et al., "Cell-Based Cardiovascular Repair", *Basic Res Cardiol*, 100, (2005),504-517.

Pera, M. F., et al, "Human Embryonic Stem Cells", *Journal of Cell Science*, 113(1), (2000),5-10.

Piedrahita, J. A., et al., "Influence of Feeder Layer Typo on the Efficiency of Isolation of Porcine Embryo-Derived Cell Lines", *Theriogenology*, 34(5), (Nov. 1990),865-877.

Pittenger, M. F., et al., "Multilineage Potential of Adult Human Mesenchymal Stem Cells", *Science*, 284 (5411), (Apr. 2, 1999), 143-147.

Prockop, D. J., "Marrow Stromal Cells as Stem Cells for Nonhematopoietic Tissues", *Science*, 276(5309), (Apr. 4, 1997), 71-74.

Prosper, F., et al., "Phenotypic and Functional Characterization of Long-Term Culture-Initiating Cells Present in Peripheral Blood Progenitor Collections of Normal Donors Treated With Granulocyte Colony-Stimulating Factor", *Blood*, 88(6), (1996),2033-2042.

Punzel, M., et al., "The Myeloid-Lymphoid Initiating Cell (ML-IC) Assay Assesses the Fate of Multipotent Human Progenitors In Vitro", *Blood*, 93(11), (Jun. 1, 1999),3750-3756.

Qi, H., et al., "Identification of Genes Responsible for Bone Differentiation From Human Bone Marrow Derived Multipotent Adult Stem Cells (MASC)", *Blood*, 96(11)(Part 1), (Nov. 16, 2000),70a-71a.

Qi, H., et al., "Identification of Genes Responsible for Osteoblast Differentiation From Human Mesodermal Progenitor Cells", *Proc. Natl. Acad. Sci. USA*, 100(6), (Mar. 18, 2003),3305-3310.

Raptis, A., et al., "Polymorhoism in CD33 and CD34 Genes: a Source of Minor Histocompatibility Antigens on Haemopoietic Progenitor Cells?", *British Journal of Haematology*, 102 (5), (1998),1354-1358.

Reddy, S., et al., "Fluorescence-Activated Sorting of Totipotent Embryonic Stem Cells Expressing Developmentally Regulated IacZ Fusion Genes", *Proc. Natl. Acad. Sci. USA*, 89(15), (1992),6721-6725.

Reffelmann, T., et al., "Cellular Cardiomyoplasty—Cardiomyocytes, Skeletal Myoblasts, or Stem Cells for Regenerating Myocardium and Treatment of Heart Failure?", *Cardiovascular Research*, 58(2), (2003),358-368.

Reinecke, H., et al., "Skeletal Muscle Stem Cells Do Not Transdifferentiate Into Cardiomyocytes After Cardiac Grafting", *J. Mol. Cell. Cardiol.*, 34(2), (2002)241-249.

Reya, T., "Stem Cells, Cancer, and Cancer Stem Cells", *Nature*, 414, (Nov. 1, 2001),105-111.

Reyes, M., et al., "Characterization of Multilineage Mesodermal Progenitor Cells in Adult Marrow", *Abstract No. 124, American Society of Hematology*, (Dec. 2001),1 pg.

Reyes, M., et al., "Characterization of Multipotent Adult Progenitor Cells, A Subpopulation of Mesenchymal Stem Cells", *Annals of the New York Academy of Science*, 938, (2001),231-235.

Reyes, M., et al., "Endotheial Cells Generated from Human Marrow Derived Mesenchymal Stem Cells (MSC)", *Abstract No. 2276, American Society for Hematology*, (Dec. 2001), 1 pg.

Reyes, M., et al., "In Vitro and In Vivo Characterization of Neural Cells Derived From Mesenchymal Stem Cells", *Abstract No. 2126, American Society for Hermatology*, (Dec. 2001), 1 pg.

Reyes, M., et al., "Origin of Endothelial Progenitors in Human Postnatal Bone Marrow", *The Journal of Clinical Investigation*, 109(3), (2002),337-346.

Reyes, M., et al., "Purification and ex vivo Expansion of Postnatal Human Marrow Mesodermal Progenitor Cells", *Blood*, 98(9), (2001),2615-2625.

Reyes, M., et al., "Skeletal Smooth and Cardiac Muscle Differentation From Single Adult Marrow Derived Mesodermal Progenitor Cells", *Abstract No. 2610, American Society for Hematology*, (Dec. 2001), 1 pg.

Reyes, M., et al., "Turning Marrow Into Brain: Generation of Blial and Neuronal Cells From Adult Bone Marrow Mesenchymal Stem Cells", *Abstract No. 1676, American Society for Hematology*, (Dec. 2001), 1 pg.

Richards, M., et al., "Human Feeders Support Prolonged Undifferentiated Growth of Human Inner Cell Masses and Embryonic Stem Cells", *Nature Biotechnology*, 20, (2002),933-936.

Rosford, et al., "The Octamer Motif Present in the Rex-1 Promoter Binds Oct-1 and Oct-3 Expressed by EC Cells and ES Cells", *Biochemical and Biophysical Research Communications*, 203(3), (1994),1795-1802.

Rosner, M. H., et al., "Oct-3 is a Maternal Factor Required for the First Mouse Embryonic Division", *Cell*, 64(6), (1991),1103-1110.

Roy, V., et al., "Expression and Function of Cell Adhesion Molecules on Fetal Liver, Cord Blood and Bone Marrow Hematopoietic Progenitors: Implications for Anatomical Localization and Developmental Stage Specific Regulation of Hematopoiesis", *Experimental Hematology*, 27(2), (1999),302-312.

Rubin, L. L., et al., "Satellite Cells in Isolated Adult Muscle Fibers in Tissue Culture", *In: Muscle Regeneration*, Mauro, A., et al., Editors, Raven Press, New York, N.Y.,(1979),281-284.

Saito, S., et al., "Bovine Embryonic Stem Cell-Like Cell Lines Cultured Over Several Passages", *Roux's Archives of Developmental Biology*, 201(3), (1992)134-141.

Sakai, T., et al., "Fetal Cell Transplantation: A Comparision of Three Cell Types", *J. Thorac. Cardiovasc. Surg.*, 118(4), (1999),715-724.

Schuldiner, M., et al., "Effects of Eight Growth Factors on the Differentiation of Cells Derived From Human Embryonic Stem Cells", *Proc. Natl. Acad. Sci. USA*, 97(21), (Oct. 10, 2000), 11307-11312.

Schwartz, R. E., "Multipotent Adult Progenitor Cells From Bone Marrow Differentiate Into Functional Hepatocyte-Like Cells", *J. Clin. Invest.*, 109(10), (May 2002), 1291-1302.

Sesragnoli, et al., "Dendritic Cell Differentiation From Hematopoietic CD34+ Progenitor Cells", *Journal of Biological Regulators and Homeostatic Agents*, 15(1), (2001),49-52.

Sims, M. M., et al., "Production of Fetuses From Totipotent Cultured Bovine Inner Cell Mass Cells", *Theriogenology*, 39, (1993),p. 313.

Smith, A., "Cell Therapy: In Search of Pluripotency", *Current Biology*, 8(22), (1998),R802-R804.

Sohn, R. L., et al., "Stem Cell Therapy for Muscular Dystrophy", *Expert Opinion Biol Ther*, vol. 4(1), (2004),1-9.

Soonpaa, M. H., et al., "Formation of Nascent Intercalated Disks Between Grafted Fetal Cardiomyocytes and Host Myocardium", *Science*, 264(5155), (Apr. 1, 1994),98-101.

Spradling, A., et al., "Stem Cells Find Their Niche", *Nature*, 414, (Nov. 1, 2001),98-104.

Steinhelper, M. E., et al., "Proliferation in vivo and in Culture of Differentiated Adult Atrial Cardiomycytes From Transgenic Mice", *American Journal of Physiology—Heart and Circulatory Physiology*, 259, (1990),H1826-1834.

Takahashi, T., et al., "Ischemia- and Cytokine-Induced Mobilization of Bone Marrow-Derived Endothelial Progenitor Cells for Neovascularization", *Nature Medicine*, 5(4), (1999),434-438.

Talbot, N. C., et al., "Alkaline Phosphatase Staining of Pig and Sheep Epiblast Cells in Culture", *Molecular Reproduction and Development*, 36(2), (1993),139-147.

Taylor, D. A., "Cell-Based Myocardial Repair: How Should We Proceed?", *Int. J. Cardiol.*, 95(Suppl. 1):, (2004),S8-S12.

Temple, S., "The Development of Neural Stem Cells", *Nature*, 414, (Nov. 1, 2001),112-117.

Terstappen, L. W., et al., "Sequential Generations of Hematopoietic Colonies Derived From Single Nonlineage-Committed CD34+CD38- Progenitor Cells", *Blood*, 77(6), (1991),1218-1227.

Thompson, L., "Fetal Transplants Show Promise", *Science*, 257(5072), (Aug. 14, 1992),868, 870.

Thomson, J. A., et al., "Embryonic Stem Cell Lines Derived From Human Blastocysts", *Science*, 282(5391), (Nov. 6, 1998),1145-1147.

Thomson, J. A., et al., "Isolation of a Primate Embryonic Stem Cell Line", *Proc. Natl. Acad. Sci. USA*, 92(17), (Aug. 15, 1995),7844-7848.

Thomson, J. A., et al., "Pluripotent Cell Lines Derived From Common Marmoset (*Callithrix jacchus*) Blastocysts", *Biology of Reproduction*, 55, (1996),254-259.

Toma, J. G., et al., "Isolation of Multipotent Adult Stem Cells From the Dermis of Mammalin Skin", *Nature Cell Biology*, 3(9), (2001),778-784.

Tomita, S., et al., "Autologous Transplantation of Bone Marrow Cells Improves Damaged Heart Function", *Circulation*, 100(19)(Suppl.), (1999),II-247-II-256.

Utrizberea, J. A., et al,, "Therapies in Muscluar Dystrophy: Current Concepts and Future Prospects", *European Neurology*, 43, (2000),127-32.

Van Stekelenburg-Hamers, A. E., et al., "Isolation and Characterization of Permanent Cell Lines From Inner Cell Mass Cells of Bovine Blastocysts", *Molecular Reproduction and Development*, 40(4), (1995),444-454.

Verfaillie, C. M., "Adult Stem Cells: Assessing the Case for Pluripotency", *Trends in Cell Biology*, 12(11), (2002),502-508.

Verfaillie, C. M., "Investigator Profile", *Journal of Hematology and Stem Cell Research*, 11, (2002),441-444.

Verfaillie, C. M., "Meeting Report on an NHLBI Workshop on Ex Vivo Expansion of Stem Cells, Jul. 29, 1999, Washington, D. C. National Heart Lung and Blood Institute", *Experimental Hematology*, 28(4). (Apr. 2000),361-364.

Verfaillie, C. M., "Optimizing Hematopoietic Stem Cell Engraftment: A Novel Role for Thrombopietin", *Journal of Clinical Investigation*, 110, (2002),303-304.

Verfaillie, C. M., "Stem Cells in Chronic Myelogenous Leukemia", *Hematol. Oncol. Clin. North. Am.*, 11(6), (1997),1079-1114.

Verfaillie, C. M., et al., "Stem Cells: Hype and Reality", *Hematology—American Society of Hematology Education Program*, (2002),369-391.

Wade, N., et al., "Scientists Herald a Versatile Adult Cell", [online]. The New York Times, Jan. 25, 2002. Retrieved from the Internet: <URL: http://query.nytimes.com/gst/fullpage.html?sec=health &res=940DEEDD163AF936A15752C0A9649C8B63>,2 pgs.

Wang, Y., et al., "Enhanced Recovery of Hematopoietic Progenitor and Stem Cells From Cultivated, Postpartum Human Placenta", *Blood*, 11(98)(Part 1),(Nov. 16, 2001),p. 183a.

Wang, J. S., et al., "The Coronary Delivery of Marrow Stromal Cells for Myocardial Regeneration: Pathophysiologic and Therapeutic Implications", *J. Thorac. Cardiovasc. Surg.*, 122(4), (2001),699-705.

Wernet, P., et al., "Detection of Unrestricted Multipotential Stem Cells in Human Cord Blood", *Blood*, 98(11)(Part 1), (Abstract #2300), (Nov. 16, 2001),p. 550a.

Westphal, S. P., "Adult Bone Marrow Eyed as Source of Stem Cells", [online]. Boston Globe, Jan. 24, 2002. [archived Feb. 6, 2002]. Retrieved from the Internet: <URL: http://www.boston.com/dailyglobe2/024/nation/Adult_bone_marrow_eyed_as_source_of stem_cells+.shtml>, 1 pg.

Westphal, S. P., "Ultimate Stem Cell Discovery", *New Scientist*, (Jan. 23, 2002), 1 pg.

Wobus, A. M., et al., "Retinoic Acid Accelerates Embryonic Stem Cell-Derived Cardiac Differentiation and Enhances Development of Ventricular Cardiomyocytes", *J. Mol. Cell. Cardiol.*, 29(6), (1997),1525-1539.

Xhou, L. J., et al., "CD14+ Blood Monocytes Can Differentiate Into Functionally Mature CD83+ Dendritic Cells", *Proc. Natl. Acad. Sci. USA*, 93, (1996),2588-2592.

Xu, C., et al., "Feeder-Free Growth of Undifferentiated Human Embryonic Stem Cells", *Nature Biotechnology*, 19(10),(2001),971-974.

Yaffe, D., et al., "Serial Passaging and Differentiation of Myogenic Cells Isolated From Dystrophic Mouse Muscle", *Nature*, 270, (1977),725-727.

Yang, Y., et al., "Enhanced Recovery of Hematopoietic Progenitor and Stem Cells From Cultivated, Postpartum Human Placenta", *Blood*, 98(11)(Part 1), (Abstract #769),(Nov. 16, 2001),p. 183a.

Yin, A. H., et al., "AC133, a Novel Marker for Human Hematopoietic Stem and Progenitor Cells", *Blood*, 90(12), (1997),5002-5012.

Zhao, L. R., et al., "Human Bone Marrow Stem Cells Exhibit Neural Phenotypes and Ameliorate Neurological Deficits After Grafting into the Ischemic Brain of Rats", *Experimental Neurology*, 174(1), (Mar. 2002),11-20.

Zhao, L. R., et al., "Immunohistochemical Identification of Multipotent Adult Progenitor Cells From Human Bone Marrow After Transplantation Into the Rat Brain", *Brain Res Brain Res Protoc.*, 11(1), (2003),38-45.

Brazelton et al., "From marrow to brain: expression of neuronal phenotypes in adult mice" Science; 290:1775-9 (2000).

Clarke el al., "Generalized potential of adult neural stem cells" Science; 288: 1660-3 (2000).

Johansson et al., "Neural stem cells in the adult human brain" Exp. Cell. Res.; 253:733-6 (1999).

Mezey et al., "Turning blood into brain: cells bearing neuronal antigens generated in vivo from bone marrow" Science; 290:1779-82 (2000).

Morshead at al., "Hematopoietic competence is a rare property of neural stem cells that may depend on genetic and epigentic alterations" Nat. Med.; 8:288-73 (2002).

Petersen et al., "Bone marrow as a potential source of hepatic oval cells" Science; 284:1168-70 (1999).

Sanchez-Ramos et al., "Adult bone marrow stromal cells differentiate into neural cells in vitro" Exp. Neurol.; 164:247-56 (2000).

Scintu et al., "Differentiation of human bone marrow stem cells into cells with a neural phenotype: diverse effects of two specific treatments" BMC Neurosci.; 7:14 (2006).

Woodbury et al., "Adult rat and human bone marrow stromal cells differentiate into neurons" J. Neurosci. Res.; 61:364-370 (2000).

Lee et al., "In vitro hepatic differentiation of human mesenchymal stem cells" Hepatology; 40:1275-1284 (Dec. 2004).

Eglitis et al., "Hematopoietic cells differentiate into both microglia and macroglia in the brain of adult mice" Proc. Natl. Acad. Sci. USA; 94:4080-85 (1997).

Kopen et al., "Marrow stromal cells migrate throughout forebrain and cerebellum, and they differentiate into astrocytes after Injecton into neonatal mouse brains" Proc. Natl. Acad. Sci. USA; 96:10711-16 (1999).

Lankford, U.S. Patent and Trademark Office, Non-final Office Action dated Apr. 3, 2007 for U.S. Appl. No. 11/238,234.

Jiang et al., "Pluripotency at mesenchymal stem cells derived from adult marrow, Supplemental information for Verfaillie Corrigendum" Nature; 418:41-49 (2002).

Verfaillie, "Letter to the Editor" Experimental Hematology; (2007).

Aldous et al., "Flawed stem cell data withdrawn" New Scientist; ( Feb. 15, 2007).

Aldous et al., "Fresh questions on stem cell findings" New Scientist; (Mar. 24, 2007).

Check "Stem cell paper corrected" Nature; 447:763 (2007) and Jiang et al., "Pluripotency of mesenchymal stem cells derived from adult bone marrow" Erratum in Nature; 447:879-880 (2007).

Chi, "Adult stem cell figure retracted" The Scientist; (Jun. 13, 2007).

Glenn, "Paper on versatility of adult stem cells comes under question" The Chronicle; (Feb. 28, 2007).

Holden, "Stem Cells. Controversial marrow cells coming into their own?" Science; 315:760-781 (2007).

Jiang et al., "Muitipotent progenitor cells can be isolated from postnatal murine bone marrow, muscle, and brain" Exp. Hematol.; 30:896-904 (2002).

Lerner et al., "Stem cell study was flawed, U panel finds" Star Tribune; (Feb. 27, 2007).

Noonan, "Limitations on the usefulness of adult stem cells" Patent Docs (Feb. 28, 2007).

Pincock, "Adult stem cell report questioned" The Scientist (Feb. 26, 2007).

Reyes el al., "Purification and ex vivo expansion of postnatal human marrow mesodermal progenitor cells" Blood; 98:2615-25 (2001).

Wang, X. et al., "Cell fusion is the principal source of bone-marrow-derived hepatocytes" Nature; 422:897-901 (2003).

Pittenger et al., "Multilineage potential of adult human mesenchymal stem cells"; Science; 284:143-147 (1999).

Serafini et al., "Hematopoietic reconstitution by multipotent adult progenitor cells: precursors to long-term hematopoietic stem cell" J. Exp. Med.; 204:129-139 (2007).

Applicants' Second Supplemental Information Disclosure Statement submitted to the USPTO in U.S. Appl. No. 10/945,528 on Oct. 3, 2008 and the accompanying Forms SB/08b.

U.S. Patent and Trademark Office, Office Action dated Jun. 24, 2005 in related U.S. Appl. No. 10/040,757.

U.S. Patent and Trademark Office, Office Action and 892 dated Jun. 27, 2008 in related U.S. Appl. No. 10/467,963.

U.S. Patent and Trademark Office, Office Action dated Oct. 15, 2009 in related U.S. Appl. No. 10/467,963.

U.S. Patent and Trademark Office, Office Action dated Apr. 7, 2008 in related U.S. Appl. No. 11/151,689.

U.S. Patent and Trademark Office, Office Action dated Jan. 4, 2006 in related U.S. Appl. No. 11/238,234.

U.S. Patent and Trademark Office, Office Action dated Aug. 29, 2006 in related U.S. Appl. No. 11/238,234.

U.S. Patent and Trademark Office, Office Action dated Apr. 3, 2007 in related U.S. Appl. No. 11/238,234.

U.S. Patent and Trademark Office, Office Action dated Oct. 7, 2008 in related U.S. Appl. No. 11/238,234.

 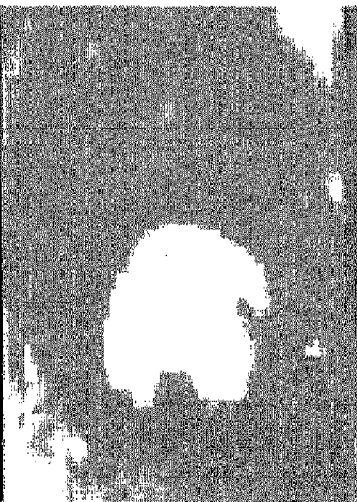 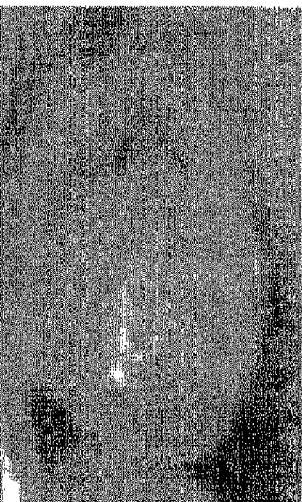
FIG. 4A  FIG. 4B  FIG. 4C
FIG. 5A  FIG. 5B

SEQUENCE LISTING

<160> NUMBER OF SEQ ID NOS: 52

<210> SEQ ID NO 1
<211> LENGTH: 22
<212> TYPE: DNA
<213> ORGANISM: Artificial Sequence
<220> FEATURE:
<223> OTHER INFORMATION: A synthetic primer

<400> SEQUENCE: 1
ggagtcatct ctggattcaa gc                                        22

<210> SEQ ID NO 2
<211> LENGTH: 22
<212> TYPE: DNA
<213> ORGANISM: Artificial Sequence
<220> FEATURE:
<223> OTHER INFORMATION: A synthetic primer

<400> SEQUENCE: 2
gctataggca gacatctccc ac                                        22

<210> SEQ ID NO 3
<211> LENGTH: 21
<212> TYPE: DNA
<213> ORGANISM: Artificial Sequence
<220> FEATURE:
<223> OTHER INFORMATION: A synthetic primer

<400> SEQUENCE: 3
ctcagggtca tgagttcaag c                                         21

<210> SEQ ID NO 4
<211> LENGTH: 19
<212> TYPE: DNA
<213> ORGANISM: Artificial Sequence
<220> FEATURE:
<223> OTHER INFORMATION: A synthetic primer

<400> SEQUENCE: 4
gtaggctcca catccagca                                            19

<210> SEQ ID NO 5
<211> LENGTH: 25
<212> TYPE: DNA
<213> ORGANISM: Artificial Sequence
<220> FEATURE:
<223> OTHER INFORMATION: A synthetic primer

<400> SEQUENCE: 5
caggcttcta tgtgctcctc atgat                                     25

<210> SEQ ID NO 6
<211> LENGTH: 24
<212> TYPE: DNA
<213> ORGANISM: Artificial Sequence
<220> FEATURE:
<223> OTHER INFORMATION: A synthetic primer

<400> SEQUENCE: 6
gttgacccag atgatgtcaa ggtg                                      24

<210> SEQ ID NO 7
<211> LENGTH: 20
<212> TYPE: DNA

```
<213> ORGANISM: Artificial Sequence
<220> FEATURE:
<223> OTHER INFORMATION: A synthetic primer

<400> SEQUENCE: 7
caggctcagg gtgtagcact                                              20

<210> SEQ ID NO 8
<211> LENGTH: 19
<212> TYPE: DNA
<213> ORGANISM: Artificial Sequence
<220> FEATURE:
<223> OTHER INFORMATION: A synthetic primer

<400> SEQUENCE: 8
gacggcctca agttgctct                                               19

<210> SEQ ID NO 9
<211> LENGTH: 22
<212> TYPE: DNA
<213> ORGANISM: Artificial Sequence
<220> FEATURE:
<223> OTHER INFORMATION: A synthetic primer

<400> SEQUENCE: 9
cccaagtgtc aactccaact ct                                           22

<210> SEQ ID NO 10
<211> LENGTH: 22
<212> TYPE: DNA
<213> ORGANISM: Artificial Sequence
<220> FEATURE:
<223> OTHER INFORMATION: A synthetic primer

<400> SEQUENCE: 10
cagcacagga cattctctct ga                                           22

<210> SEQ ID NO 11
<211> LENGTH: 19
<212> TYPE: DNA
<213> ORGANISM: Artificial Sequence
<220> FEATURE:
<223> OTHER INFORMATION: A synthetic primer

<400> SEQUENCE: 11
ctgttccctt cccaacagg                                               19

<210> SEQ ID NO 12
<211> LENGTH: 19
<212> TYPE: DNA
<213> ORGANISM: Artificial Sequence
<220> FEATURE:
<223> OTHER INFORMATION: A synthetic primer

<400> SEQUENCE: 12
ttgatgactg gcacgctct                                               19

<210> SEQ ID NO 13
<211> LENGTH: 19
<212> TYPE: DNA
<213> ORGANISM: Artificial Sequence
<220> FEATURE:
<223> OTHER INFORMATION: A synthetic primer

<400> SEQUENCE: 13
ctggcctgcc tgacaagta                                               19
```

```
<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
atctcaacga gtgggtgtcc                                                  20

<210> SEQ ID NO 15
<211> LENGTH: 22
<212> TYPE: DNA
<213> ORGANISM: Artificial Sequence
<220> FEATURE:
<223> OTHER INFORMATION: A synthetic primer

<400> SEQUENCE: 15
agagaactcc atgaagaggc tg                                               22

<210> SEQ ID NO 16
<211> LENGTH: 22
<212> TYPE: DNA
<213> ORGANISM: Artificial Sequence
<220> FEATURE:
<223> OTHER INFORMATION: A synthetic primer

<400> SEQUENCE: 16
cttgtcaatg gaagagaggg ac                                               22

<210> SEQ ID NO 17
<211> LENGTH: 21
<212> TYPE: DNA
<213> ORGANISM: Artificial Sequence
<220> FEATURE:
<223> OTHER INFORMATION: A synthetic primer

<400> SEQUENCE: 17
gggaagactg tgaacaccaa g                                                21

<210> SEQ ID NO 18
<211> LENGTH: 20
<212> TYPE: DNA
<213> ORGANISM: Artificial Sequence
<220> FEATURE:
<223> OTHER INFORMATION: A synthetic primer

<400> SEQUENCE: 18
ggttggcact gatgatctga                                                  20

<210> SEQ ID NO 19
<211> LENGTH: 22
<212> TYPE: DNA
<213> ORGANISM: Artificial Sequence
<220> FEATURE:
<223> OTHER INFORMATION: A synthetic primer

<400> SEQUENCE: 19
gacagtcaac accaagaggg tc                                               22

<210> SEQ ID NO 20
<211> LENGTH: 22
<212> TYPE: DNA
<213> ORGANISM: Artificial Sequence
<220> FEATURE:
<223> OTHER INFORMATION: A synthetic primer
```

```
<400> SEQUENCE: 20
gatgatctgg tcctccagag tg                                              22

<210> SEQ ID NO 21
<211> LENGTH: 22
<212> TYPE: DNA
<213> ORGANISM: Artificial Sequence
<220> FEATURE:
<223> OTHER INFORMATION: A synthetic primer

<400> SEQUENCE: 21
ggtacactga caacgaacca ga                                              22

<210> SEQ ID NO 22
<211> LENGTH: 22
<212> TYPE: DNA
<213> ORGANISM: Artificial Sequence
<220> FEATURE:
<223> OTHER INFORMATION: A synthetic primer

<400> SEQUENCE: 22
cattaaggga gcagctatca cc                                              22

<210> SEQ ID NO 23
<211> LENGTH: 22
<212> TYPE: DNA
<213> ORGANISM: Artificial Sequence
<220> FEATURE:
<223> OTHER INFORMATION: A synthetic primer

<400> SEQUENCE: 23
cgcagacctg atggatttca ag                                              22

<210> SEQ ID NO 24
<211> LENGTH: 21
<212> TYPE: DNA
<213> ORGANISM: Artificial Sequence
<220> FEATURE:
<223> OTHER INFORMATION: A synthetic primer

<400> SEQUENCE: 24
cgcttcttca ttcggctcac t                                               21

<210> SEQ ID NO 25
<211> LENGTH: 22
<212> TYPE: DNA
<213> ORGANISM: Artificial Sequence
<220> FEATURE:
<223> OTHER INFORMATION: A synthetic primer

<400> SEQUENCE: 25
ggtgctctac aacctcaagg ag                                              22

<210> SEQ ID NO 26
<211> LENGTH: 19
<212> TYPE: DNA
<213> ORGANISM: Artificial Sequence
<220> FEATURE:
<223> OTHER INFORMATION: A synthetic primer

<400> SEQUENCE: 26
gatggagaag atgtggggc                                                  19

<210> SEQ ID NO 27
<211> LENGTH: 22
<212> TYPE: DNA
```

<213> ORGANISM: Artificial Sequence
<220> FEATURE:
<223> OTHER INFORMATION: A synthetic primer

<400> SEQUENCE: 27
gagaggagaa agagagctcc aa                                            22

<210> SEQ ID NO 28

<400> SEQUENCE: 28

000

<210> SEQ ID NO 29
<211> LENGTH: 44
<212> TYPE: DNA
<213> ORGANISM: Artificial Sequence
<220> FEATURE:
<223> OTHER INFORMATION: A synthetic primer

<400> SEQUENCE: 29
ggtgttctca tcctgggtta ctggtgttct catcctgggt tact                    44

<210> SEQ ID NO 30
<211> LENGTH: 20
<212> TYPE: DNA
<213> ORGANISM: Artificial Sequence
<220> FEATURE:
<223> OTHER INFORMATION: A synthetic primer

<400> SEQUENCE: 30
acctgaggaa cagagggaaa                                               20

<210> SEQ ID NO 31
<211> LENGTH: 21
<212> TYPE: DNA
<213> ORGANISM: Artificial Sequence
<220> FEATURE:
<223> OTHER INFORMATION: A synthetic primer

<400> SEQUENCE: 31
ctgaagaaat ctccctgttg g                                             21

<210> SEQ ID NO 32
<211> LENGTH: 18
<212> TYPE: DNA
<213> ORGANISM: Artificial Sequence
<220> FEATURE:
<223> OTHER INFORMATION: A synthetic primer

<400> SEQUENCE: 32
cgaactgcag acgctgat                                                 18

<210> SEQ ID NO 33
<211> LENGTH: 20
<212> TYPE: DNA
<213> ORGANISM: Artificial Sequence
<220> FEATURE:
<223> OTHER INFORMATION: A synthetic primer

<400> SEQUENCE: 33
tcagctcctc ctcctctttc                                               20

<210> SEQ ID NO 34
<211> LENGTH: 22
<212> TYPE: DNA
<213> ORGANISM: Artificial Sequence

```
<220> FEATURE:
<223> OTHER INFORMATION: A synthetic primer

<400> SEQUENCE: 34
ctttctccct tccagaagga ct                                              22

<210> SEQ ID NO 35
<211> LENGTH: 22
<212> TYPE: DNA
<213> ORGANISM: Artificial Sequence
<220> FEATURE:
<223> OTHER INFORMATION: A synthetic primer

<400> SEQUENCE: 35
tggatctcct ctgtctgttc ct                                              22

<210> SEQ ID NO 36
<211> LENGTH: 18
<212> TYPE: DNA
<213> ORGANISM: Artificial Sequence
<220> FEATURE:
<223> OTHER INFORMATION: A synthetic primer

<400> SEQUENCE: 36
caggaggtcg tggacaag                                                   18

<210> SEQ ID NO 37
<211> LENGTH: 18
<212> TYPE: DNA
<213> ORGANISM: Artificial Sequence
<220> FEATURE:
<223> OTHER INFORMATION: A synthetic primer

<400> SEQUENCE: 37
aggtcagccc cggaaaag                                                   18

<210> SEQ ID NO 38
<211> LENGTH: 22
<212> TYPE: DNA
<213> ORGANISM: Artificial Sequence
<220> FEATURE:
<223> OTHER INFORMATION: A synthetic primer

<400> SEQUENCE: 38
cttcctggaa cagcagaaca ag                                              22

<210> SEQ ID NO 39
<211> LENGTH: 20
<212> TYPE: DNA
<213> ORGANISM: Artificial Sequence
<220> FEATURE:
<223> OTHER INFORMATION: A synthetic primer

<400> SEQUENCE: 39
gctgttgcca gtgagttggt                                                 20

<210> SEQ ID NO 40
<211> LENGTH: 20
<212> TYPE: DNA
<213> ORGANISM: Artificial Sequence
<220> FEATURE:
<223> OTHER INFORMATION: A synthetic primer

<400> SEQUENCE: 40
actgcactca ccctgaggac                                                 20
```

<210> SEQ ID NO 41
<211> LENGTH: 20
<212> TYPE: DNA
<213> ORGANISM: Artificial Sequence
<220> FEATURE:
<223> OTHER INFORMATION: A synthetic primer

<400> SEQUENCE: 41
gctggacagc atctccatct                                         20

<210> SEQ ID NO 42
<211> LENGTH: 20
<212> TYPE: DNA
<213> ORGANISM: Artificial Sequence
<220> FEATURE:
<223> OTHER INFORMATION: A synthetic primer

<400> SEQUENCE: 42
cttccatccc aacttctcca                                         20

<210> SEQ ID NO 43
<211> LENGTH: 20
<212> TYPE: DNA
<213> ORGANISM: Artificial Sequence
<220> FEATURE:
<223> OTHER INFORMATION: A synthetic primer

<400> SEQUENCE: 43
ctgggaaagc ataagcatgt                                         20

<210> SEQ ID NO 44
<211> LENGTH: 22
<212> TYPE: DNA
<213> ORGANISM: Artificial Sequence
<220> FEATURE:
<223> OTHER INFORMATION: A synthetic primer

<400> SEQUENCE: 44
caccagatcc agtcctacac ct                                      22

<210> SEQ ID NO 45
<211> LENGTH: 19
<212> TYPE: DNA
<213> ORGANISM: Artificial Sequence
<220> FEATURE:
<223> OTHER INFORMATION: A synthetic primer

<400> SEQUENCE: 45
gcaatgttgt cctgtagcc                                          19

<210> SEQ ID NO 46
<211> LENGTH: 21
<212> TYPE: DNA
<213> ORGANISM: Artificial Sequence
<220> FEATURE:
<223> OTHER INFORMATION: A synthetic primer

<400> SEQUENCE: 46
gtgatgctgg tgctgagtat g                                       21

<210> SEQ ID NO 47
<211> LENGTH: 19
<212> TYPE: DNA
<213> ORGANISM: Artificial Sequence
<220> FEATURE:
<223> OTHER INFORMATION: A synthetic primer

<400> SEQUENCE: 47

```
gtgatggcat ggacggtgg                                                    19

<210> SEQ ID NO 48
<211> LENGTH: 20
<212> TYPE: DNA
<213> ORGANISM: Artificial Sequence
<220> FEATURE:
<223> OTHER INFORMATION: A synthetic primer

<400> SEQUENCE: 48
agcaaagacc ccaacgagaa                                                   20

<210> SEQ ID NO 49
<211> LENGTH: 15
<212> TYPE: DNA
<213> ORGANISM: Artificial Sequence
<220> FEATURE:
<223> OTHER INFORMATION: A synthetic primer

<400> SEQUENCE: 49
ggcggcggtc acgaa                                                        15

<210> SEQ ID NO 50
<211> LENGTH: 22
<212> TYPE: DNA
<213> ORGANISM: Artificial Sequence
<220> FEATURE:
<223> OTHER INFORMATION: A synthetic primer

<400> SEQUENCE: 50
cgcgatcaca tggtcctgct gg                                                22

<210> SEQ ID NO 51
<211> LENGTH: 18
<212> TYPE: DNA
<213> ORGANISM: Artificial Sequence
<220> FEATURE:
<223> OTHER INFORMATION: A synthetic primer

<400> SEQUENCE: 51
cgacggcaac tacaagac                                                     18

<210> SEQ ID NO 52
<211> LENGTH: 21
<212> TYPE: DNA
<213> ORGANISM: Artificial Sequence
<220> FEATURE:
<223> OTHER INFORMATION: A synthetic primer

<400> SEQUENCE: 52
tagttgtact ccagcttgtg c                                                 21
```

MAPC GENERATION OF MUSCLE

RELATED APPLICATIONS/PATENTS

This application is a continuation of U.S. application Ser. No. 10/945,528 (filed Sep. 20, 2004) now abandoned; which is a continuation-in-part of U.S. application Ser. No. 10/048,757 (filed Aug. 21, 2002) now U.S. Pat. No. 7,015,037; which is a U.S. National Stage Application of PCT/US2000/21387 (filed Aug. 4, 2000) (Publication No. WO 01/11011 published on Feb. 15, 2001); which claims priority under 35 U.S.C. §119(e) from U.S. Provisional Application No. 60/147,324 (filed Aug. 5, 1999) and U.S. Provisional Application No. 60/164,650 (filed Nov. 10, 1999). U.S. application Ser. No. 10/945,528 also claims priority under 35 U.S.C. §119(e) from U.S. Provisional Application No. 60/504,125 (filed Sep. 19, 2003). This application is also a continuation-in-part of U.S. application Ser. No. 12/907,495 (filed Oct. 19, 2010); which is a continuation of U.S. application Ser. No. 10/467,963 (filed Jan. 5, 2004) now U.S. Pat. No. 7,838,289 (Publication No. U.S. 2004/0107453 published on Jun. 3, 2004); which is a U.S. National Stage Application of PCT/US2002/04652 (filed Feb. 14, 2002) (Publication No. WO 02/064748 published on Aug. 22, 2002); which claims priority under 35 U.S.C. §119(e) from U.S. Provisional Application No. 60/268,786 (filed Feb. 24, 2001); U.S. Provisional Application No. 60/269,062 (filed Feb. 15, 2001); U.S. Provisional Application No. 60/310,625 (filed Aug. 7, 2001); and U.S. Provisional Application No. 60/343,836 (filed Oct. 25, 2001). This application claims priority to all of the above applications. The above applications and publications are incorporated by reference herein.

STATEMENT OF RIGHTS TO INVENTIONS MADE UNDER FEDERALLY SPONSORED RESEARCH

This work was funded by United States Grant No. RO1-HL67932 from the National Institutes of Health. The government may have certain rights to this invention.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

FIELD OF THE INVENTION

The present invention relates to methods of increasing striated muscle function in a subject comprising providing multipotent adult progenitor cells (MAPCs) to existing striated muscle and generating new striated muscle. Increased striated muscle function, and preferably mass, is provided by exogenous MAPCs, and/or endogenous stem or progenitor cells, including MAPCs. Other aspects of the invention are described in or are obvious from the following disclosure, and are within the ambit of the invention.

BACKGROUND OF THE INVENTION

Cardiac and skeletal muscle are categorized as striated muscle, having actin and myosin filaments aligned in orderly arrays to form a series of contractile units which give the cells a striated appearance. Numerous types of muscular disorders affecting striated muscle share an underlying pathology characterized by loss of muscle mass and function. This would include cardiac disorders such as myocardial infarction, certain forms of idiopathic non-ischemic cardiomyopathies, degenerative muscular diseases (e.g., muscular dystrophies and myasthenia gravis) and even traumatic physical injuries to striated muscle. Therapeutic approaches which contribute to restoration of muscle mass and function will be useful in the treatment of all disorders characterized by this common pathology.

Myocardial infarction (MI) is characterized by the death of myocytes, by coagulative necrosis, myocytolysis, contraction band necrosis, or apoptosis, resulting from a critical imbalance between the oxygen supply and demand of the myocardium. The most common cause of MI is coronary artery thrombosis following the rupture of atheromatous plaques in epicardial blood vessels resulting in regional myocardial ischemia. Though once strictly defined as a lack of blood flow, the modern definition of ischemia emphasizes both the imbalance between oxygen supply and demand while also emphasizing the inadequate removal of metabolic waste products. Impaired oxygen delivery results in a reduction in oxidative-phosphorylation resulting in dependence on anaerobic glycolysis for the production of high-energy phosphates. This shift in metabolism produces excess lactate, which accumulates in the myocardium. Impaired ATP production and acidosis prevails with a resultant decline in myocardial contractility, which may further reduce blood delivery past the obstruction in the coronary vessel. Similarly, ischemia reperfusion injury without total occlusion can also cause cardiac damage The exposure of the contents of the plaque to the basement membrane following plaque rupture ultimately results in vessel blockage culminating from a series of events including platelet aggregation, thrombus formation, fibrin accumulation, and vasospasm. Total occlusion of the vessel for more than 4-6 hours results in irreversible myocardial necrosis. Ultimately, death and morbidity due to myocardial infarction is the result of fatal dysrhythmia or progressive heart failure. Progressive heart failure is chiefly the result of insufficient muscle mass or due to improper function of the heart muscle, which can be caused by various conditions including but not limited to hypertension, and is therefore the focus of cellular based therapy.

All current strategies for the treatment of myocardial infarction focus on limiting myocyte death. Annually in the United States, 500,000 patients undergo angioplasty with stent placement, 400,000 will undergo coronary artery bypass, while an unknown additional number of patients will be treated by thrombolytic therapy. Overall prognosis is highly variable and depends on a number of factors related to the timing and nature of intervention, success of the intervention in limiting infarct size, and post-MI management. Better prognosis is associated with early reperfusion, inferior wall infarct, preserved LV function, short-term and long-term treatment with beta-blockers, aspirin, and ACE inhibitors. In contrast, poor prognosis is associated with delay in reperfusion or unsuccessful reperfusion.

One approach that has received recent attention focuses on repopulation and engraftment of the injured myocardium by transplantation of healthy cells, which is otherwise known as cellular cardiomyoplasty (Reffelmann, T., and Kloner, R. A. (2003) *Cardiovasc Res.* 58(2): 358-68). Many cell types that might replace necrotic tissue and minimize regional scarring have been considered. Cells that have already committed to a specific lineage, such as satellite cells, cardiomyocytes, primary myocardial cell cultures, fibroblasts, and skeletal myoblasts have been readily used in cellular cardiomyoplasty with limited success in restoring damaged tissue and improving cardiac function (Menasche, P. (2003) *Cardiovasc Res.* 58(2): 351-7; Etzion, S., et al, (2001) *J Mol Cell Cardiol.* 33(7): 1321-30; Sakai, T. et al, (1999) *J. Thorac. Cardiovasc. Surg.* 118(4): 715-24).

Cardiogenic progenitors are precursor cells that have committed to the cardiac lineage, but have not differentiated into cardiac muscle. Cardiomyocytes are the cells that comprise the heart, also known as cardiac muscle cells. Use of cardiomyocytes in the repair of cardiac tissue has been proposed, however, this approach is hindered by an inability to obtain sufficient quantities of cardiomyocytes for the repair of large areas of infarcted myocardium. Doubt has also been cast over the incorporation and tissue-specific function of intra-cardiac grafts derived from cardiomyocytes, even when harvested from embryonic sources (Etzion, S., et al, (2001) *J. Mol. Cell. Cardiol.* 33(7): 1321-30). Intra-cardiac grafts using this cell type can be successfully grafted and are able to survive in the myocardium after permanent coronary artery occlusion and extensive infarction. However, rat-engrafted embryonic cardiomyocytes attenuate, but do not fully reverse left ventricular dilatation and prevention of wall thinning. While survival is improved during 8 weeks of follow-up, the implanted cells did not develop into fully differentiated myocardium. Surprisingly, they remained isolated from the host myocardium by scar tissue and did not result in an improvement in systolic function over time. (Etzion, S. et al, (2001) *J. Mol. Cell. Cardiol.* 33(7): 1321-30).

The term muscular dystrophy describes a group of diseases characterized by hereditary progressive muscle weakness and degeneration. Duchenne muscular dystrophy (DMD) and Becker muscular dystrophy (BMD) are allelic, lethal degenerative muscle diseases with an incidence of 1:3500 male births (Clemens et al, In: Current Neurology, Appel, Ed., Mosby-Year Book, Chicago, Ill., Vol. 14, pp. 29-54 (1994)). In DMD, mutations in the dystrophin gene usually result in the absence of dystrophin, a cytoskeletal protein in skeletal and cardiac muscle. In BMD, dystrophin is usually expressed in muscle, but at a reduced level and/or as a shorter, internally deleted form, resulting in a milder phenotype. No effective treatment is available for DMD or BMD at this time.

Congenital muscular dystrophy (CMD) is a clinically and genetically heterogeneous group of autosomal recessive neuromuscular disorders of early onset. In the classic form of CMD, clinical manifestations are limited to skeletal muscle with no clinical involvement of the central nervous system (CNS) although changes in the white matter have been detected by MRI. The histological changes in muscle biopsies consist of connective tissue proliferation, large variation in the size of the muscle fibers as well as some necrotic and regenerating fibers.

The myotonic muscular dystrophy (DM) disease is the most common adult muscular dystrophy in man with a prevalence of 1 in 10,000. The disorder is inherited in an autosomal dominant manner with variable expression of symptoms from individual to individual within a given family. Furthermore, the phenomenon of anticipation (increasing disease severity over generations) is well documented for DM. This is particularly evident when an affected mother transmits the gene for the disease to her offspring. These offspring have a high incidence of mental retardation and profound infantile myotonia. Adult patients with DM manifest a pleiotropic set of symptoms including myotonia, cardiac arrhythmias, cataracts, frontal baldness, hypogonadism, and other endocrine dysfunctions. Other muscular dystrophies include limb-girdle muscular dystrophy, facioscapulohumeral (FSH) muscular dystrophy and the like.

Myasthenia gravis is a neuromuscular conduction defect that is responsible for progressive weakening of skeletal muscle strength, involvement of the extraocular muscles and levator palpebral and results in diplopia and ptosis. Diplopia, in particular, can be disabling. Myasthenia gravis is defined as a condition typified by a fluctuating condition of easy fatigability of voluntary muscles aggravated by exertion, emotion, menstruation or infection, and relieved, both subjectively and objectively, by rest and anti-cholinesterase drugs.

Like myocardial infarction, degenerative muscular diseases such as muscular dystrophies and myasthenia gravis affect striated muscle and share an underlying pathology characterized by loss of muscle mass or proper function. Treatments focusing on myocardial repair through autologous cellular substitution have also been proposed for various degenerative muscular diseases.

Satellite cells are undifferentiated skeletal myoblasts and represent a unique myogenic stem cell population with a committed fate, which is capable of regenerating injured skeletal muscle (Menasche, P. (2003) *Cardiovasc. Res.* 58(2): 351-7; Menasche, P. et al, (2001) Lancet 357(9252): 279-80; Campion, D. R. (1984) *Int. Rev. Cytol.* 87: 225-5). Autologous skeletal myoblasts are the best-characterized cell type that could be considered for myocardial repair. While successful delivery of autologous skeletal myoblasts to the heart can be achieved by direct intra-myocardial injection or via intra-arterial routes, and despite their ability to survive, adapt within the cardiac microenvironment, and improve myocardial performance in experimental animal models, fundamental differences exist between skeletal myoblasts and cardiomyocytes (Reffelmann, T., and Kloner, R. A. (2003) *Cardiovasc Res.* 58(2): 358-68). These differences extend to morphology, mechanism of electromechanical coupling, and response to injury, which influences the successful incorporation of skeletal myoblasts into the host myocardium (Kessler, P. D. and Byrne, B. J. (1999) *Annu. Rev. Physiol.* 61: 219-42). Moreover, engrafted skeletal myoblasts assume a slow-twitch phenotype in vivo, which only partially mirrors the cardiac phenotype (Reinecke, H. et al, (2002) *J. Mol. Cell. Cardiol.* 34(2): 241-9).

The ideal candidate for cellular renewal of the myocardium is likely to be a less committed, self-renewing stem cell that can undergo full myogenic differentiation. Such a cell population might be found in the adult bone marrow. It is now accepted that cell populations isolated from bone marrow and expanded in vitro represents a potential source of undifferentiated cells that can give rise to multiple cell types. Three such examples that have been utilized experimentally are hematopoietic stem cells (HSCs), mesenchymal stem cells (MSCs), and endothelial progenitor cells (EPCs).

Whole bone marrow contains various populations of multipotent mesenchymal stem cells that are derived from somatic mesoderm and are involved in the self-maintenance and repair of various mesenchymal tissues. These cells can be induced in vitro and in vivo to differentiate into fat, cartilage, bone, cardiac and skeletal muscle. Bone marrow MSCs have been demonstrated to engraft and differentiate into cardiac tissue in a rat model of cardiac infarction (Wang, J. S. et al, (2001) *J. Thorac. Cardiovasc. Surg.* 122(4): 699-705). In some instances of bone marrow MSC engraftment, ventricular function was enhanced and bone marrow MSCs expressed a cardiac phenotype, however, the cells accumulated in the center of the scar tissue and were unlikely to have incorporated with host myocardium or to have contributed to contractile function (Tomita S., et al, (1999) *Circulation* 100 [suppl II]: 11-247-II-256). The MSCs induced angiogenesis in the host scar tissue and this may have contributed to improvement of cardiac function by replenishing blood flow to hibernating host myocardium (Tomita S. et al, (1999) *Circulation* 100 [suppl II]: II-247-II-256). Other studies also found similar results, wherein cardiac function did improve, but ultimately, engraftment of MSCs with host tissues was extremely low (Hughes, S., (2002) *J. Pathol.* 197(4): 468-78).

Bone marrow is also a known source of endothelial progenitor cells (EPCs). Circulating bone marrow-derived EPCs have been isolated from bone marrow and home to sites of vasculogenesis and angiogenesis, where they contribute to new vessel formation following infarction. EPCs have been used in rats, where a high level of engraftment was achieved (Asahara T. et al, (1997) *Science* 275(5302): 964-7). Replenishment of the vascular supply influenced the remodeling process and there was reduced scar tissue formation and improvement of cardiac function (Takahashi, T. et al, (1999) *Nat Med.* 5(4): 434-8). Further, compared with control animals, there was evidence that neovascularization contributed to myocardial salvage of non-infarcted tissue (Kocher, A. A. et al, (2001) *Nat Med.* 7(4): 430-6).

Work by Drs. Donald Orlic and Piero Anversa have demonstrated that populations of multipotent hematopoietic stem cells (HSCs) could give rise to vascular endothelium, smooth muscle cells, and cardiomyocytes. In the study by Orlic et al, large myocardial infarctions were induced by coronary ligation in mice (Orlic D., et al, (2001) *Nature* 410(6829): 701-5). Within hours of injury, enriched lin$^-$, c-kit$^+$ bone marrow cells were isolated from transgenic male donor mice and injected into the undamaged contracting tissue surrounding the infarct. These injected cells were able to migrate to the damaged myocardium, proliferate, transdifferentiate, and form a band of new myocardium and associated vasculature. The injected cells had successfully differentiated into myocardial tissue, confirming that the new cardiomyocytes represented maturing cells in the process of attaining functional competence, also expressed cardiac-specific transcription factors (Orlic D. et al, (2001) *Ann. NY Acad. Sci.* 938: 221-9; discussion 229-30). Repair and improved cardiac performance were obtained in 40% of the injected mice, however the associated mortality with this procedure was high. Other studies have determined that administration of cytokines such as stem cell factor and granulocyte-colony stimulating factor can mobilize and allow HSCs from adult male mice to home to and generate de novo myocardium and vascular structures in the infarcted heart and improve cardiac hemodynamics (Hughes, S. (2002) *J. Pathol.* 197(4): 468-78).

The most primitive cell type that has been used in cellular cardiomyoplasty is the embryonic stem cell (ES). Pluripotent ES cells can be derived from the inner cell mass of the blastocyst, while embryonic germ (EG) cells have been isolated from primordial germ cells. Undifferentiated stem cell lines have the capacity to differentiate in vitro into cells derived from all three primary germ layers, and can differentiate spontaneously into cardiomyocytes, endothelial cells, and vascular smooth muscle cells. Several groups have demonstrated the ability of ES cells to form stable intra-cardiac grafts. Klug and others engrafted genetically modified differentiated murine ES-derived cardiomyocytes into the left ventricular free wall of dystrophic mdx recipient mice (Klug, M. G. et al, (1996) *J. Clin. Invest.* 98(1): 216-24). These ES-derived cardiomyocytes were able to survive in damaged myocardium and improve cardiac function. A drawback of the cardiac engraftment studies to date is that pure and reproducible populations of ES-derived cardiomyocytes were not obtained. ES-derived cardiomyocyte cultures used for example, by Klug et al exhibited heterogeneous immunoreactivity to atrial natriuretic factor, which suggests that the ventricular cardiomyocyte sub-population for intra-cardiac grafting may well be a heterogeneous population (Klug, M. G. et al, (1996) *J. Clin. Invest.* 98(1): 216-24). Furthermore, ES-derived cardiomyocytes eventually become post-mitotic, and thus, the proliferative capacity of these cells in vivo is likely to be limited (Klug, M. G. et al, (1996) *J. Clin. Invest.* 98(1): 216-24). Generating sufficient numbers of these ES-derived cardiomyocytes may prove to be an obstacle, as well as the low regeneration of the myocardium by these cells. Yield was shown to be improved in vitro by addition of retinoic acid or overexpression of the GATA-4 transcription factor, however it is yet to be determined if these strategies work in vivo (Wobus, A. M. et al, (1997) *J. Mol. Cell. Cardiol.* 29(6): 1525-39; Grepin, C. et al, (1997) *Development* 124 (12): 2387-95). Another potential drawback of the use of embryonic stem cells is their ability to form teratomas, which can then turn into life-threatening pathologies (Takada, T. et al, (2002) *Cell Transplant.* 11(7): 631-5).

While advances in the field of cardiac transplantation and cardiomyoplasty have been achieved with the advent of stem cell technology, a population of cells that are able to effectively engraft damaged myocardium and restore cardiac function without improper differentiation to other contaminating cell types is still highly desired. While pluripotent ES cells offer the promise of functional plasticity and the ability to differentiate into any cell type in vitro, extensive experimentation in vivo is still necessary to properly direct the formation of incorporated, functional cardiac tissue at the site of injury without improper differentiation to form teratomas or other non-cardiac cell types. Multipotent tissue-specific cells that have already committed to a distinct lineage, such as HSCs, MSCs, and EPCs, have also produced encouraging results. However use of these cells often results in incomplete engraftment and a failure to restore cardiac function over time. Therefore, attractive candidates would include an undifferentiated, preferably adult, stem cell population that has not committed to a specific lineage.

SUMMARY OF THE INVENTION

Loss of function and/or mass in striated muscle (e.g., cardiac and skeletal muscle) can arise, for example, by physical damage or disease related damage (e.g., genetic or acquired disease). Stem cell technology has made cellular myoplasty a realistic treatment for restoring or enhancing striated muscle function or mass. While tissue-specific stem cells and embryonic stem cells have afforded limited, yet encouraging results, it has now been demonstrated that a population of multipotent adult stem cells, previously named multipotent adult progenitor cells (MAPCs), are capable of effectively restoring or enhancing striated muscle function in damaged tissues over time. Therefore, the present invention relates to methods of improving function and/or mass in striated muscle tissue by administering MAPCs. MAPCs can engraft into the tissue to be treated in both healthy and in damaged sites.

In one embodiment, the present invention comprises a process for providing striated muscle cells in a subject comprising administering MAPCs to the subject in an amount effective to produce striated muscle cells.

In another embodiment, the present invention comprises methods of providing skeletal muscle cells in a subject comprising administering an amount of MAPCs to the subject effective to generate new skeletal muscle.

In another embodiment, the present invention comprises methods of providing cardiac muscle cells in a subject comprising administering an amount of MAPCs to the subject effective to generate new cardiac muscle.

In another embodiment, the present invention comprises methods of increasing striated muscle mass in a subject comprising providing an amount of MAPCs to generate new striated muscle.

The methods can further comprise preliminary measures of isolating and expanding a population of MAPCs.

In preferred embodiments, engraftment of MAPCs is within cardiac and skeletal muscle.

In yet another embodiment, the present invention comprises administration of MAPCs to a subject in need thereof in the presence of cytokines to optionally enhance homing of MAPCs to damaged or abnormal striated muscle tissues, and to enhance differentiation of MAPCs into cells of the myogenic lineage (e.g., cardiomyocytes, myocytes, myoblasts and terminally differentiated muscle cells).

In another aspect, the present invention comprises methods of increasing skeletal muscle tissue mass in a subject comprising providing an amount of MAPCs effective to generate new skeletal muscle.

In another aspect, the present invention comprises methods of increasing cardiac muscle tissue mass in a subject comprising providing an amount of MAPCs effective to generate new cardiac muscle.

In yet another aspect, the present invention comprises methods of increasing striated or skeletal muscle function in a subject comprising providing MAPCs to existing striated or skeletal muscle tissue in an amount effective to generate new muscle.

Cells integrating within, and therefore contributing to, the generation of new muscle tissue can include endogenous stem or progenitor cells (e.g., MAPCs), recruited stem or progenitor cells, exogenous MAPCs and combinations thereof.

In one embodiment, the present invention comprises methods of improving cardiac function in a subject comprising administering an amount of MAPCs to the subject effective to generate new cardiac muscle.

Evaluation of cardiac function can be monitored using various well-known imaging techniques such as myocardial perfusion imaging, gated cardiac blood-pool imaging, first-pass ventriculography, right-to-left shunt detection, positron emission tomography, single photon emission computed tomography, magnetic resonance imaging, harmonic phase magnetic resonance imaging, echocardiography, and myocardial perfusion reserve imaging.

Administered MAPCs may contribute to generation of new tissue by differentiating into muscle cells in vivo. Alternatively, or in addition, administered MAPCs may contribute to generation of new tissue by secreting cellular factors that aid in homing and recruitment of endogenous MAPCs or other stem cells, such as hematopoietic or mesenchymal stem cells or other more differentiated cells such as skeletal myoblasts, cardiac myoblasts and myocytes. Alternatively, or in addition, MAPCs may secrete factors that act on endogenous stem or progenitor cells in the target tissue causing them to differentiate in the target site, thereby enhancing function.

In a preferred embodiment, MAPC-based therapies can be used to treat damage resulting from disease states including congestive heart failure, coronary artery disease, myocardial infarction, myocardial ischemia, effects of atherosclerosis or hypertension, cardiomyopathy, cardiac arrhythmias, muscular dystrophy, muscle mass abnormalities, muscle degeneration, myasthenia gravis, infective myocarditis, drug- and toxin-induced muscle abnormalities, hypersensitivity myocarditis, autoimmune endocarditis, and congenital heart disease.

MAPCs can be administered to a subject by a variety of methods known in the art, such as but not limited to, surgical intramyocardial injection, transendocardial injection, intracoronary injection, transvascular injection, intramuscular injection, and intravenous injection. MAPCs may be administered, within or in proximity to, the site requiring new muscle cells, mass, or enhanced function. Alternatively they can be administered at a remote location.

Preferably, the striated muscle is cardiac muscle.

Other aspects of the invention are described in or are obvious from the following disclosure, and are within the ambit of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference.

FIG. 4 depicts representative images from one imaging session used in Cine analysis for global function assessment (FIG. 4A). True FISP sequences for determination of Myocardial Perfusion Reserve are provided at an early (FIG. 4B) and late (FIG. 4C) phase of contrast injection.

FIG. 5 depicts delayed contrast injection imaging to document relative sizes of myocardial ischemia (shown by arrow, FIG. 5B), compared with gross pathology (FIG. 5A).

DETAILED DESCRIPTION OF THE INVENTION

Definitions

Figure 1:
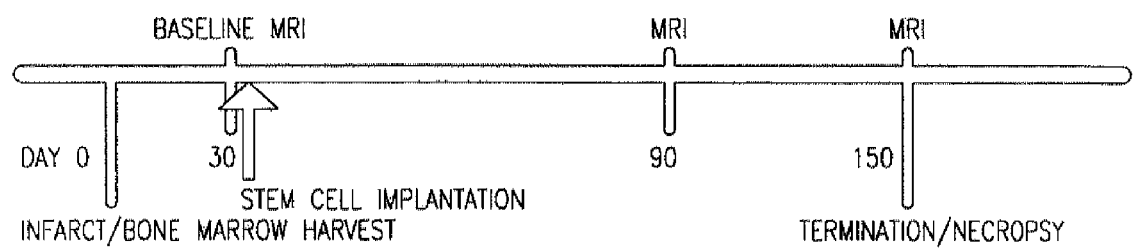
FIG. 1 depicts the study time line, indicating injection time points as well as subsequent MRI follow-up studies.

As used herein, the terms below are defined by the following meanings.

"MAPC" is an acronym for a multipotent adult progenitor cell. It refers to a multipotent adult stem cell that can give rise to cell lineages of all three germ layers (i.e., endoderm, mesoderm and ectoderm) upon differentiation. Like embryonic stem cells, the MAPCs express, in human MAPCs, oct3A (oct 3/4), rex-1, rox-1 and sox-2, and they may express SSEA-4.

"Multipotent" refers to the ability to give rise to more than one differentiated cell type. MAPCs have extensive multipotency, in that they can give rise to cell lineages of all three germ layers (i.e., endoderm, mesoderm and ectoderm) upon differentiation.

"Pluripotent" refers to the ability to give rise to all somatic cell types found in the embryo and adult animal. However, it is noted that pluripotent cells cannot differentiate into trophectoderm cells, which are cells responsible for implantation of the blastocyst to the uterine wall.

"Expansion" refers to the propagation of a cell or cells without differentiation.

"Progenitor cells" are cells produced during differentiation of a stem cell that have some, but not all, of the characteristics of their terminally differentiated progeny. Defined progenitor cells, such as "cardiac progenitor cells," are committed to a lineage, but not to a specific or terminally differentiated cell type. The term "progenitor" as used in the acronym "MAPC" does not limit these cells to a particular lineage.

"Cardiomyocyte" refers to cells that comprise the heart, also known as cardiac muscle cells.

"Cardiogenic progenitors" are precursor cells that have committed to the cardiac lineage, but have not differentiated into cardiac muscle.

A "myoblast" is a mononucleated, undifferentiated muscle precursor cell.

"Self-renewal" refers to the ability to produce replicate daughter stem cells having differentiation potential that is identical to those from which they arose. A similar term used in this context is "proliferation."

"Striated muscle" refers to muscle having actin and myosin filaments aligned in orderly arrays to form a series of contractile units which give the cells a striated appearance. Types of striated muscle include skeletal and cardiac muscle.

"Engraft" refers to the process of cellular contact and incorporation into an existing tissue of interest in vivo.

"Cytokines" refer to cellular factors that induce or enhance cellular movement, such as homing of MAPCs or other stem cells, progenitor cells or differentiated cells such as skeletal myoblasts, cardiac myoblasts, myocytes, and the like.

"Differentiation factors" refer to cellular factors, preferably growth factors or angiogenic factors that induce lineage commitment.

A "Subject" is a vertebrate, preferably a mammal, more preferably a human. Mammals include, but are not limited to, humans, farm animals, sport animals, and pets. Subjects in need of treatment by methods of the present invention include those suffering from a loss of function in striated muscle as a result of physical or disease related damage. Disease states characterized by loss of striated muscle mass and/or function, and that benefit from methods of the present invention include, but are not limited to, congestive heart failure, coronary artery disease, myocardial infarction, myocardial ischemia, atherosclerosis, cardiomyopathy, cardiac arrhythmias, muscular dystrophies, muscle mass abnormalities, muscle degeneration, myasthenia gravis, infective myocarditis, drug- and toxin-induced muscle abnormalities, hypersensitivity myocarditis, autoimmune endocarditis, and congenital heart disease.

The terms "comprises", "comprising", and the like can have the meaning ascribed to them in U.S. Patent Law and can mean "includes", "including" and the like.

Administration of MAPCs

MAPCs can be administered to a subject by a variety of methods known in the art. Preferably, administration is through injection, including but not limited to, surgical intramyocardial injection, transendocardial injection, intracoronary injection, transvascular injection, intramuscular injection, and intravenous injection.

Surgical myocardial injection is an invasive approach that may be particularly suitable to patients who are undergoing concurrent surgical procedures. The injection process can be performed under direct visualization, thereby allowing evaluation by direct inspection of potential target zones. Not all areas of the myocardium can be readily accessed with this approach.

Transendocardial injection primarily involves a catheter system known as NOGA. The injection catheter incorporates the mapping capabilities of the system. This provides a means by which tissues with different degrees of viability and ischemia can be mapped in detail, allowing therapy to be precisely targeted (e.g. at the border zone of an infarct). NOGA catheters can be used alongside detection techniques such as magnetic resonance imaging (MRI), echocardiogram (EKG), or computed tomographic techniques such as positron emission tomography (PET) or single photon emission computed tomography (SPECT).

Introcoronary injection is particularly well suited for delivery of cells to a specific coronary territory. It is less complex than transendocardial delivery, and because of the segmental nature of coronary artery disease, may be more practical than other techniques. Where retention of cells in the target area is at issue, this technique is especially suited for treating relatively intense ischemia. The quantity of cells and time of infusion can be carefully monitored to avoid coronary flow impairment and myocardial cell necrosis.

Intravenous injection is the simplest method of cell administration, however a greater degree of dependence on homing of the stem cells is required for them to reach the tissue of interest (e.g., myocardium). Carefully controlled dosing, which is readily determined by one skilled in the art, enhances this method of administration.

Certain cytokines can alter or affect the migration of MAPCs or their differentiated counterparts to the site of damaged muscle tissue. "Homing" of stem cells to the injured muscle tissues concentrates the implanted cells in an environment favorable to their growth and function. In more acutely ischemic situations, the stem cells can be administered either peripherally or locally through the circulatory system. When the homing signals may be less intense, as may be the case for chronic ischemic or nonischemic cardiomyopathies, injection of the cells directly into the cardiac muscle may produce a more favorable outcome. Pre-treatment of a patient with cytokine(s) to promote homing is another alternative contemplated in the methods of the present invention.

Cytokines include, but are not limited to, stromal cell derived factor-1 (SDF-1), stem cell factor (SCF) and granulocyte-colony stimulating factor (G-CSF). Cytokines also include any which promote the expression of endothelial adhesion molecules, such as ICAMs, VCAMs, and others, which facilitate the homing process.

Differentiation of MAPCs to a phenotype characteristic of muscular tissues can be enhanced when differentiation factors are employed. Differentiation factors promoting muscle formation include, but are not limited to vascular endothelial growth factor (VEGF), fibroblast growth factors (e.g., FGF4, FGF8, bFGF) Wnt11, DKK1, ascorbic acid, isoproterenol and endothelin.

Viability of newly forming tissues can be enhanced by angiogenesis. Differentiation factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol, nicotinic amide.

Factors that decrease apoptosis can also promote the formation of new striated muscle. Factors that decrease apoptosis include, but are not limited to, β-blockers, angiotensin-converting enzyme inhibitors (ACE inhibitors), carvedilol, angiotensin II type 1 receptor antagonists, caspase inhibitors, cariporide, and eniporide.

Exogenous factors (e.g., cytokines, differentiation factors and anti-apoptosis factors) can be administered prior to, after or concomitantly with MAPCs. For example, a form of concomitant administration would comprise combining a factor of interest in the MAPC suspension media prior to administration. Doses or for administrations are variable, may include an initial administration followed by subsequent administrations; but nonetheless, can be ascertained by the skilled artisan, from this disclosure, the documents cited herein, and the knowledge in the art.

A method to potentially increase cell survival is to incorporate MAPCs or other cells of interest into a biopolymer or synthetic polymer. Depending on the patient's condition, the site of injection might prove inhospitable for cell seeding and growth because of scarring or other impediments. Examples of biopolymer include, but are not limited to, cells mixed with fibronectin, fibin, fibrinogen, thrombin, collagen, and proteoglycans. This could be constructed with or without included cytokines or differentiation factors. Additionally, these could be in suspension but residence time at sites subjected to flow would be nominal. Another alternative is a three-dimension gel with cells entrapped within the interstices of the cell biopolymer admixture. Again differentiation factors or cytokines could be included within the cells. These could be deployed by injection via various routes described herein, via cardiac catheters or other surgical procedures.

An issue concerning the therapeutic use of stem cells is the quantity of cells necessary to achieve an optimal effect. In current human studies of autologous mononuclear bone marrow cells, empirical doses ranging from 1 to $4 \times 10^7$ cells have been used with encouraging results. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and most preferably, $3 \times 10^7$ stem cells and optionally, 50 to 500 µg/kg per day of a cytokine can be administered to a human subject. However, the precise determination of what would be considered an effective dose may be based on factors individual to each patient, including their size, age, size of the infarct or other muscular damage, and amount of time since the damage occurred. Therefore, dosages can be readily ascertained by those skilled in the art from this disclosure and the knowledge in the art.

Another issue regarding the use of stem cells is the purity of the population. Bone marrow cells, for example, comprise mixed populations of cells, which can be purified to a degree sufficient to produce a desired effect. Those skilled in the art can readily determine the percentage of MAPCs in a population using various well-known methods, such as fluorescence activated cell sorting (FACS). Preferable approximate ranges of purity in populations comprising MAPCS are 50-55%, 55-60%, 60-65%, and 65-70%; more preferably 70-75%, 75-80%, 80-85%; and most preferably 85-90%, 90-95%, and 95-100%. Purity of MAPCs can be determined according to the cell surface marker profile or mRNA expression in cells in the population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, MAPCs can be administered initially, and thereafter maintained by further administration of MAPCs. For instance, MAPCs can be administered by one method of injection, and thereafter further administered by a different or the same type of method. For example, MAPCs can be administered by surgical myocardial injection to bring cardiovascular function to a suitable level. The patient's levels can then maintained, for example, by intravenous injection, although other forms of administration, dependent upon the patient's condition, can be used.

It is noted that human subjects are treated generally longer than the canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and drug effectiveness and the subject being treated.

Examples of compositions comprising MAPCs include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs as described in the present invention.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, can be ascertained by the skilled artisan, from this disclosure, the documents cited herein, and the knowledge in the art.

Stem Cells of the Present Invention

MAPCs are multipotent adult stem cells that can give rise to cell lineages of all three germ layers (i.e., endoderm, mesoderm and ectoderm) upon differentiation.

MAPCs are further characterized as cells that constitutively express Oct-4 and high levels of telomerase (Jiang, Y. et al, 2002). MAPCs derived from human, mouse, rat or other mammals appear to be the only normal, non-malignant, somatic cell (i.e., non-germ cell) known to date to express very high levels of telomerase even in late passage cells. The telomeres are extended in MAPCs and they are karyotypically normal. Because MAPCs injected into a mammal can migrate to and assimilate within multiple organs, MAPCs are self-renewing stem cells. As such, they have utility in the repopulation of organs, either in a self-renewing state or in a differentiated state compatible with the organ of interest. They have the capacity to replace cell types that could have been damaged, died, or otherwise might have an abnormal function because of genetic or acquired disease.

Human MAPCs (also known as multipotent adult stem cells (MASCs)) are described in PCT/US00/21387 (published as WO 01/11011) and PCT/US02/04652 (published as WO 02/064748), the contents of which are incorporated herein by reference for their characterization of MAPCs. MAPCs have been identified in other mammals. Murine MAPCs, for example, are also described in PCT/US00/21387 (published as WO 01/11011) and PCT/US02/04652 (published as WO 02/064748).

Methods of MAPC isolation and maintenance in cell culture are described in PCT/US00/21387 (published as WO 01/11011) and PCT/US02/04652 (published as WO 02/064748), and these methods are incorporated herein by reference. MAPCs can be isolated from multiple sources, including bone marrow, muscle, brain, spinal cord, blood or skin. To isolate MAPCs, bone marrow mononuclear cells can be derived from bone marrow aspirates, which can be obtained by standard means known to those of skill in the art (see, for example, Muschler, G. F., et al., J. Bone Joint Surg. Am. (1997) 79(11): 1699-709, Batinic, D., et al., Bone Marrow Transplant. (1990) 6(2): 103-7).

MAPCs are present within the bone marrow (or other organs, such as liver and brain), but do not express the common leukocyte antigen CD45 or erythroblast specific glycophorin-A (GlyA). In humans the mixed population of cells can be subjected to a Ficoll Hypaque separation. Cells can then be subjected to negative selection using anti-CD45 and anti-Gly-A antibodies, depleting the population of $CD45^+$ and $GlyA^+$ cells, and recovering the remaining approximately 0.1% of marrow mononuclear cells. Cells can also be plated in fibronectin coated wells and cultured as described below for 2-4 weeks after which the cells are depleted of $CD45^+$ and $GlyA^+$ cells. Alternatively, positive selection can be employed to isolate cells using a combination of cell-specific markers, such as the leukemia inhibitory factor (LIF) receptor. Both positive and negative selection techniques are known to those of skill in the art, and numerous monoclonal and polyclonal antibodies suitable for negative selection purposes are also known in the art (see, for example, LeukocZe Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch, et al., J. Immunol. Methods (1983) 56: 269 (immunoaffinity chromatography), and Wysocki and Sato, Proc. Natl. Acad. Sci. (USA) (1978) 75: 2844 (fluorescence-activated cell sorting).

Recovered CD45-/GlyA-cells can be plated onto culture dishes coated with 5-ng/ml (preferably about 7-10 ng/ml) serum fibronectin or other appropriate matrix coating. Cells can be maintained in Dulbecco Minimal Essential Medium (DMEM) or other appropriate cell culture medium, supplemented with 10 ng/ml (preferably about 5-15 ng/ml) platelet-derived growth factor-BB (PDGF-BB), 1-50 ng/ml (preferably about 5-15 ng/ml) epidermal growth factor (EGF), 1-50 ng/ml (preferably about 5-15 ng/ml) insulin-like growth factor (IGF), or 100-10,000 IU (preferably about 1,000 IU) LIF, with 100 to $10-8$ M dexamethasone or other appropriate steroid, 2-10 gg/ml linoleic acid, and 0.05-0.15 gM ascorbic acid. Other appropriate media include, for example, MCDB, MEM, IMDM, and RPML Cells can either be maintained without serum, in the presence of 1-2% fetal calf serum, or, for example, in 1-2% human AB serum or autologous serum. Preferred maintenance density is around 2,000 cells/cm$^2$.

Methods for Genetically Altering MAPCs

Cells isolated by the method described herein can be genetically modified by introducing DNA or RNA into the cell by a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus for example; (2) chemical transfer, including calcium phosphate transfection and DEAE dextran transfection methods; (3) membrane fusion transfer, using DNA-loaded membrane vesicles such as liposomes, red blood cell ghosts, and protoplasts, for example; and (4) physical transfer techniques, such as microinjection, electroporation, or direct "naked" DNA transfer.

MAPCs can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) for expression in specific cell compartments (including but not limited to the cell membrane).

Calcium phosphate transfection, which relies on precipitates of plasmid DNA/calcium ions, can be used to introduce plasmid DNA containing a target gene or polynucleotide into isolated or cultured MAPCs. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the cells of the present invention are isolated cells, microinjection can be particularly effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. This technique has been used effectively to accomplish germline modification in transgenic animals.

Cells of the present invention can also be genetically modified using electroporation. The target DNA or RNA is added to a suspension of cultured cells. The DNA/RNA-cell suspension is placed between two electrodes and subjected to an electrical pulse, causing a transient permeability in the cell's outer membrane that is manifested by the appearance of pores across the membrane. The target polynucleotide enters the cell through the open pores in the membrane, and when the electric field is discontinued, the pores close in approximately one to 30 minutes.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin® (Life Technologies, Inc.), which is commercially available. Lipofectin®, for example, is a mixture of the cationic lipid N-[1-(2,3-dioleyloyx)propyl]-N-N-N-trimethyl ammonia chloride and DOPE. Delivery of linear DNA, plasmid DNA, or RNA can be accomplished either in vitro or in vivo using liposomal delivery, which may be a preferred method due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus envelope (VSV-G), in the method of Abe, A., et al. (J. Virol. (1998) 72: 6159-6163).

Gene transfer techniques which have been shown effective for delivery of DNA into primary and established mammalian cell lines using lipopolyamine-coated DNA can be used to introduce target DNA into MAPCs. This technique is generally described by Loeffler, J. and Behr, J. (Methods in Enzymology (1993) 217: 599-618).

Microprojectile gene transfer can also be used to transfer genes into MAPCs either in vitro or in vivo. The basic procedure for microprojectile gene transfer was described by J. Wolff (Gene Therapeutics (1994) at page 195). Briefly, plasmid DNA encoding a target gene is coated onto microbeads, usually 1-3 micron sized gold or tungsten particles. The coated particles are placed onto a carrier sheet inserted above a discharge chamber. Once discharged, the carrier sheet is accelerated toward a retaining screen. The retaining screen forms a barrier which stops further movement of the carrier sheet while allowing the polynucleotide-coated particles to be propelled, usually by a helium stream, toward a target surface, such as a tissue mass formed of differentiated MAPCs. Microparticle injection techniques have been described previously, and methods are known to those of skill in the art (see, for example, Johnston, S. A., et al., Genet. Eng. (NY) (1993) 15: 225-236; Williams, R. S., et al., Proc. Natl. Acad. Sci. USA (1991) 88: 2726-2730; Yang, N. S., et al., Proc. Natl. Acad. Sci. USA (1990) 87: 9568-9572).

Signal peptides can be attached to plasmid DNA (Sebestyen, et al. Nature Biotech. (1998) 16: 80-85) to direct the DNA to the nucleus for more efficient expression.

Viral vectors can be used to genetically alter MAPCs of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are effective for transducing rapidly-dividing cells, although a number of retroviral vectors have been developed to effectively transfer DNA into non-dividing cells as well (Mochizuki, H., et al., J. Virol. (1998) 72:8873-8883). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector which is ecotropic, xenotropic, or amphotropic, providing a degree of specificity for retroviral vector systems.

A retroviral DNA vector is generally used with the packaging cell line to produce the desired target sequence/vector combination within the cells. Briefly, a retroviral DNA vector is a plasmid DNA which contains two retroviral LTRs positioned about a multicloning site and SV40 promoter so that a first LTR is located 5' to the SV40 promoter, which is operationally linked to the target gene sequence cloned into the multicloning site, followed by a 3' second LTR. Once formed, the retroviral DNA vector can be transferred into the packaging cell line using calcium phosphate-mediated transfection, as previously described. Following approximately 48 hours of virus production, the viral vector, now containing the target gene sequence, is harvested.

Targeting of retroviral vectors to specific cell types was demonstrated by Martin, F., et al. (Martin, F., et al., J. Virol. (1999) 73: 6923-6929), who used single-chain variable fragment antibody directed against the surface glycoprotein high-molecular-weight melanoma-associated antigen fused to the amphotropic murine leukemia virus envelope to target the vector to deliver the target gene to melanoma cells. Where targeted delivery is desired, as, for example, when differentiated cells are the desired objects for genetic alteration, retroviral vectors fused to antibody fragments directed to the specific markers expressed by each cell lineage differentiated from the MAPCs of the present invention can be used to target delivery to those cells.

Lentiviral vectors are also used to genetically alter cells of the invention. Many such vectors have been described in the literature and are known to those of skill in the art (Salmons, B. and Gunzburg, W. H., "Targeting of Retroviral Vectors for Gene Therapy," Hum. Gene Therapy (1993) 4:129-141). These vectors have been effective for genetically altering human hematopoietic stem cells (Sutton, R., et al., *J. Virol.* (1998) 72: 5781-5788). Packaging cell lines have been described for lentivirus vectors (Kafri, T., et al., *J. Virol.* (1999) 73: 576-584; Dull, T., et al., *J. Virol.* (1998) 72: 8463-8471).

Adenoviral vectors have high transduction efficiency, can incorporate DNA inserts up to 8 Kb, and can infect both replicating and differentiated cells. A number of adenoviral vectors have been described in the literature and are known to those of skill in the art (Davidson, B. L., et al., *Nature Genetics* (1993) 3: 219-223; Wagner, E., et al., *Proc. Natl. Acad. Sci. USA* (1992)89:6099-6103). Methods for inserting target DNA into an adenovirus vector are known to those of skill in the art of gene therapy, as are methods for using recombinant adenoviral vectors to introduce target DNA into specific cell types (Wold, W., Adenovirus Methods and Protocols, Humana Methods in Molecular Medicine (1998), Blackwell Science, Ltd.).

Adenovirus vectors are also available that provide targeted gene transfer and stable gene expression using molecular conjugate vectors, constructed by condensing plasmid DNA containing the target gene with polylysine, with the polylysine linked to a replication-incompetent adenovirus. (Schwarzenberger, P., et al., *J. Virol.* (1997) 71: 8563-8571)

Alphavirus vectors, particularly the Sindbis virus vectors, are also available for transducing the cells of the present invention. These vectors are commercially available (Invitrogen, Carlsbad, Calif.) and have been described in, for example, U.S. Pat. No. 5,843,723, as well as by Xiong, C., et al. (Xiong, C., et al., *Science* (1989) 243:1188-1191), Bredenbeek, P. J., et al. (*J. Virol.* (1993) 67: 6439-6446), and Frolov, I., et al. (*Proc. Natl. Acad. Sci. USA* (1996) 93: 11371-11377).

Successful transfection or transduction of target cells can be demonstrated using genetic markers, in a technique that is known to those of skill in the art. The green fluorescent protein of *Aequorea victoria*, for example, has been shown to be an effective marker for identifying and tracking genetically modified hematopoietic cells (Persons, D., et al., *Nature Medicine* (1998) 4: 1201-1205). Alternative selectable markers include the β-Gal gene, the truncated nerve growth factor receptor, and drug selectable markers (including but not limited to NEO, MTX, hygromycin).

Culture Conditions for MAPCs

Initially, MAPCs are maintained and allowed to expand in culture medium that is well established in the art and commercially available from the American Type Culture Collection (ATCC). Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. It is within the skill of one in the art to modify or modulate concentrations of media and media supplements as necessary for the cells used. It will also be apparent that many media are available as a low-glucose formulation, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Additional supplements can also be used advantageously to supply the cells with the necessary trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies important cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability, and expansion of stem cells. In many cases, feeder cell layers are not necessary to keep the stem cells in an undifferentiated, proliferative state, as leukemia inhibitory factor (LIF) has anti-differentiation properties. Often, supplementation of a defined concentration of LIF is all that is necessary to maintain stem cells in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II, and type IV collagen, concanavalin A, chondroitin sulfate, fibronectin, "superfibronectin" and fibronectin-like polymers, gelatin, laminin, poly-D and poly-L-lysine, thrombospondin, and vitronectin.

The maintenance conditions of stem cells can also contain cellular factors that allow stem cells, such as MAPCs, to remain in an undifferentiated form (i.e., able to form cells of more than one germ layer). It is advantageous under conditions where the cell must remain in an undifferentiated state of self-renewal for the medium to contain epidermal growth factor (EGF), platelet derived growth factor (PDGF), leukemia inhibitory factor (LIF), and combinations thereof. It is apparent to those skilled in the art that supplements that allow the cell to self-renew but not differentiate must be removed from the culture medium prior to differentiation.

Stem cell lines and other fastidious cells often benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Methods of identifying and subsequently separating differentiated cells from their undifferentiated counterparts can be carried out by methods well known in the art. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes (i.e. formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the invention envisions the use of FACS to identify and separate cells based on cell-surface antigen expression.

Diseases and Conditions Treatable By MAPCs

Numerous types of muscular disorders affecting striated muscle share the same underlying pathology, which is characterized by loss of muscle mass and/or function. This would include cardiac disorders such as myocardial infarction, degenerative muscular diseases (e.g., muscular dystrophies and myasthenia gravis) and even traumatic physical injuries to striated muscle. By contributing to restoration of muscle mass and/or function, methods of the present invention will be useful in the treatment of all disorders characterized by this common pathology.

The primary advantage of MAPC-based therapies is the replacement of functional cells. In the case of degenerative myocardial disease, MAPCs provides for both myocyte replacement and stimulation of angioneogenisis. Improved cardiac function can be indicated, for example, by increased perfusion. This therapy can be used as a stand-alone therapy or in conjunction with revascularization therapies. MAPCs offer the advantage of forming vascular structures to furnish and supply blood to the emerging cardiac muscle mass.

In one embodiment, the present invention comprises methods of increasing cardiac function in a subject by administering a suitable amount of MAPCs to the subject, wherein MAPCs incorporate into existing cardiac tissues and generate new cardiac muscle.

Cardiac diseases that would benefit from MAPC-based therapies include, but are not limited to, congestive heart failure, coronary artery disease, myocardial infarction, myocardial ischemia, atherosclerosis, cardiomyopathy, cardiac arrhythmias, muscle mass abnormalities, and congenital heart disease.

Myocardial infarction (MI) is characterized by the death of myocytes, by coagulative necrosis, myocytolysis, contraction band necrosis, or apoptosis, resulting from a critical imbalance between the oxygen supply and demand of the myocardium. The most common cause of MI is coronary artery thrombosis following the rupture of atheromatous plaques in epicardial blood vessels resulting in regional myocardial ischemia. Scar formation in the infracted region impairs cardiac function.

Cardiac injury, such as MI, promotes tissue responses that enhance myogenesis using implanted MAPCs. Thus, administration of MAPCs can, for example, reduce the degree of scar formation, augment ventricular function and compensate for weakened cardiac muscle, thereby improving cardiac function. New muscle is thereby created within an infarcted myocardial segment. Preferably, MAPCs can be directly infiltrated into the zone of infarcted tissue.

MAPCs, as well as damaged cardiac tissues, secrete cytokines that have beneficial effects, including recruitment of reparative cells (e.g., MAPCs, hematopoietic, mesenchymal stem cells) to the damaged tissue by "homing" mechanisms and modulation of inflammatory processes. Homing of cells that can advantageously repair myocardium, such as MAPCs described in this disclosure, can be preferentially induced by co-administration of cytokines. MAPCs can also promote angiogenesis, which further enhances tissue repair.

In the past, the prevention of progression to end stage congestive heart failure was believed to preventable only by minimizing loss of myocyte mass. Indeed, left ventricular dysfunction is the strongest predictor of negative outcome following MI. Current treatment focuses on limiting myocyte death, but offer little to replace those myocytes that have already been destroyed. Additionally, other forms of heart failure resulting from cell death/loss not associated with ischemia can not be corrected by additional perfusion, but instead require restoration of functional muscle mass. These diseases include but are not limited to: correction of congenital abnormalities, infective myocarditis induced by viral means (HIV, Coxsackieviruses A and B), protozoa (Chagas Disease), bacteria, and idiopathic cardiomyopathies. In addition, drugs or toxins, such as those used in chemotherapy can also induce myocyte death. These include but are not limited to, doxirubicin, adriamycin, and catecholamines. Bacterial toxins can also cause death of muscle tissues. Hypersensitivity myocarditis and autoimmune endocarditis is another disease that can be treated advantageously using the methods of the present invention. SLE and Sarcoidosis may also be treated using progenitor cell-based therapies.

MAPC-based therapies are not limited to improvement of cardiac pathology, but can be extended to any type of degenerative muscular disorder in which the primary pathology is loss of striated muscle mass and/or function. This would include, but is not limited to, muscular dystrophies, trauma, and myasthenia gravis. Thus, in another embodiment, the present invention comprises methods of increasing striated muscle tissue mass by contacting a suitable amount of MAPCs with existing striated muscle tissue and generating viable striated muscle tissue.

Detection of Myocardial Engraftment

Engraftment and repopulation of striated muscle tissue by evaluating muscle function can be monitored using various well-known imaging techniques such as scintigraphy, myocardial perfusion imaging, gated cardiac blood-pool imaging, first-pass ventriculography, right-to-left shunt detection, positron emission tomography, single photon emission computed tomography, magnetic resonance imaging, harmonic phase magnetic resonance imaging, echocardiography, and myocardial perfusion reserve imaging.

Cardiac scintigraphy evaluates myocardial perfusion and/or function to detect physiologic and anatomic abnormalities of the heart. There are five major classes of cardiac scintigraphy: myocardial perfusion imaging, gated cardiac blood-pool imaging, first-pass cardiac imaging, myocardial infarction imaging, and right-to-left shunt evaluation (American College of Radiology Standard for the Performance of Cardiac Scintigraphy).

Myocardial perfusion imaging is primarily used to detect the presence, location, and extent of coronary artery disease by evaluating the physiologic significance or sequelae of known or suspected coronary artery stenosis, monitoring the effects of treatment of coronary artery disease, including revascularization and medical therapy. Myocardial perfusion imaging is also useful for detecting acute myocardial infarction and prognosis after infarction, for evaluating the viability of dysfunctional myocardium, for determining the risk of myocardial events, and for evaluating ventricular function.

Myocardial perfusion imaging currently uses thallium-201 as a tracer. Thallium-201 is recommended when the purpose of the study is to assess myocardial viability due to its ability to redistribute. Imaging is routinely started within 10 minutes after injection. Redistribution images are obtained 2-4 hours after injection, with or without the additional reinjection of 1.0 mCi of thallium. When assessing myocardial viability, additional information may be gained by obtaining 24-hour delayed images. Other sequences, such as rest and delayed redistribution imaging, may also give useful information about myocardial viability.

Other radiotracers commonly used are technetium-99m sestamibi and technetium-99m tetrafosmin. Sestamibi distributes according to regional myocardial perfusion. Unlike thallium, very little redistribution occurs. Measurement of regional myocardial perfusion during stress and rest requires two separate intravenous injections. The stress injection should be given 1-2 minutes prior to cessation of exercise. Tetrafosmin distributes according to regional myocardial blood flow. Procedures are similar to that of sestamibi, and one-day total dosages of up to 40 mCi may be used.

Exercise-induced or pharmacologically induced cardiac stress can also be advantageously used to monitor hemodynamics during myocardial perfusion imaging. For patients who are physically able to exercise, the desired endpoint is a heart rate of at least 85% of the age-predicted maximum heart rate. The patient must be monitored frequently for abnormal changes in blood pressure, marked ST changes on an echocardiogram, development of serious arrhythmias, or severe chest pain.

Pharmacologic cardiovascular stress may be induced with dipyridamole, adenosine, or dobutamine. Dipyramidole can be infused intravenously in a dosage of 0.14 mg/kg/min for 4 minutes (total dosage=0.56 mg/kg). Its duration of action is between 30 minutes and 1 hour. The radiopharmaceutical (i.e. thallium-201) should be injected 2-4 minutes after the end of the dipyridamole infusion. Dipyramidole has a variety of side effects, such as chest pain, headache, dizziness, hypotension, nausea, flushing, and dyspnea. Aminophylline (1-2 mg/kg) must be immediately available for intravenous injection and should be given to reverse significant side effects. Adenosine may also be given intravenously in a dosage of 0.14 mg/kg/min over 6 minutes (3 minutes prior to injection of the radiopharmaceutical and continued for 3 minutes thereafter). Because of the extremely short mechanism of action of adenosine, injection of the radiopharmaceutical must occur during the adenosine infusion. Side effects are very short lived, often eliminating the need for aminophylline. Dobutamine is also infused intravenously. Its duration of effect is short, with a half-life of approximately 2 minutes. A typical protocol involves the graduated infusion of increasing amounts of dobutamine over time, beginning with 5-10 mcg/kg/min each step, with a maximum dose rate of 40 mcg/kg/min.

Gated cardiac blood-pool imaging quantifies the parameters of ventricular function, such as ejection fraction, wall motion, ventricular volume, cardiac output, and diastolic function. It is useful for detecting the presence, location, and extent of coronary artery disease, as well as assesses whether congestive heart failure is due to ischemic or nonischemic causes. Gated cardiac blood-pool imaging also evaluates any potential effects of valvular abnormalities. Technetium-99m labeled autologous red blood cells, labeled by a variety of methods, are most commonly used. Technetium-99m labeled high specific activity human serum albumin may also be used as a blood-pool imaging radiopharmaceutical. Exercise, when performed, usually consists of graded levels of work performed on a bicycle ergometer with simultaneous acquisition of gated images. These are commonly obtained for 2-3 minutes during each level of exercise by imaging after heart rate equilibration, which usually occurs in 30-60 seconds. The endpoint may be achievement of a desired predefined work level of percentage of MPHR, anginal symptoms, significant ST depression or other electrocardiogram abnormality, or physical inability to continue.

First-pass cardiac imaging, also known as first-pass ventriculography, calculates left and right ventricular ejection fractions, assesses wall motion abnormalities, and quantifies left-to-right cardiac shunts, as well as measures cardiac output and absolute ventricular chamber volumes. Technetium-99m labeled red blood cells may be used, as well as other technetium-99m labeled radiopharmaceuticals, such as pertechnetate, diethylenetriamine pentaacetic acid, sestamibi, or high-specific activity human serum albumin. Injection technique is critically important. Rapid injection of a small volume of the radiotracer into a large proximal vein (e.g. external jugular) or through large-gauge intravenous access in an antecubital vein followed by an instantaneous saline flush is necessary for optimal results, especially when measuring left-to-right shunts. The size of cardiac and extra-cardiac left-to-right shunts also may be measured by assessing first transit pulmonary time-activity curves. Computer programs, such as gamma variate analysis, are applied to pulmonary curves to determine pulmonary to systemic blood-flow ratio (QP/QS).

Myocardial infarction imaging diagnoses and assesses the location and extent of acutely infarcted myocardium, while right-to-left shunt evaluation detects and quantifies right-to-left shunts using radiolabeled particles, such as technetium-99m labeled macroaggregation albumin (MAA). Myocardial infarction imaging, or infarct avid imaging, utilizes technetium-99m pyrophosphate injected intravenously. Immediate or delayed imaging may help differentiate infarct from blood pool in such patients. At least three images, anterior, LAO, and left lateral, are acquired on a scintillation camera equipped with a high-resolution collimator. SPECT imaging may help to differentiate blood-pool activity from myocardial uptake and may detect abnormalities not present on planar imaging (see description of SPECT imaging elsewhere in this disclosure).

Positron Emission Tomography (PET) and Single Photon Emission Computed Tomography (SPECT) are imaging techniques that rely on similar principles to produce their images, however important differences in instrumentation, radiochemistry, and experimental applications are dictated by inherent differences in their respective physics of photon emission.

Unstable nuclides that possess an excess number of protons may take one of two approaches in an effort to reduce their net nuclear positivity. In one radioactive decay scheme, a proton is converted to a neutron and a particle called a positron is emitted (Hoffman, E. J., and Phelps, M. E. New York: Raven Press; 1986: 237-286; Sorenson, J. A., and Phelps, M. E. Philadelphia: W.B. Saunders; 1987). Of identical mass but opposite charge, positrons are the antimatter equivalent of electrons. When ejected from the nucleus, a positron collides with an electron, resulting in the annihilation of both particles and the release of energy. Two γ photons are produced, each of equivalent energy and opposite trajectory (generally 180° apart).

The unique spatial signature of back-to-back photon paths is exploited by PET scanners in locating the source of an annihilation event, a method known as coincidence detection (Hoffman, E. J., and Phelps, M. E. New York: Raven Press; 1986: 237-286; Links, J. M. New York: Raven Press; 1990: 37-50). PET (and SPECT) scanners employ scintillation detectors made of dense crystalline materials (e.g., bismuth germanium oxide, sodium iodide, or cesium fluoride), that capture the high-energy photons and convert them to visible light. This brief flash of light is converted into an electrical pulse by an adjacent photomultiplier tube (PMT). The crystal and PMT together make up a radiation detector. A PET camera is constructed such that opposing detectors are electronically connected. Thus, when separate scintillation events in paired detectors coincide, an annihilation event is presumed to have occurred at some point along an imaginary line between the two. This information is used to reconstruct images using the principles of computed tomography. Conversely, single events are ignored. Although it is conceivable that two unrelated photons from spatially separate annihilation events might reach opposing detectors in unison, these accidental coincidences are much less frequent than true ones. Nevertheless, random coincidences constitute a source of background noise in PET images (Hoffman E J et al. *J Comput Assist Tomogr* (1981); 5:391-400; Hoffman, E. J., and Phelps, M. E. New York: Raven Press; (1986): 237-286; Links, J. M. New York: Raven Press; (1990): 37-50).

The intrinsic limitations of PET derive from the nature of positron decay and the principle of coincidence detection. Specifically, PET recognizes the site of positron annihilation, which does not necessarily coincide with the site of radioactive decay. Annihilation often occurs some distance away from the positron's origin. The distance separating these two events, decay and annihilation, depends on the average kinetic energy of the positron as it leaves the nucleus, and varies according to the specific isotope involved (Phelps M E, et al. 1975). In addition, if the positron is not entirely at rest at annihilation, photons will be emitted at an angle slightly different than 180°. Taken together, remote positron annihilation and photon non-colinearity place a theoretical limit on PET's achievable spatial resolution (Links J M. New York: Raven Press; (1990): 37-50).

Isotopes that decay by electron capture and/or γ emissions can be directly detected by SPECT. Certain proton-rich radionuclides, such as $^{123}I$ and $^{99m}Tc$, may instead capture an orbiting electron, once again transforming a proton to a neutron (Sorenson J A, and Phelps M E. Philadelphia: W.B. Saunders; 1987). The resulting daughter nucleus often remains residually excited. This meta-stable arrangement subsequently dissipates, thereby achieving a ground state and producing a single γ photon in the process. Because γ photons are emitted directly from the site of decay, no comparable theoretical limit on spatial resolution exists for SPECT. However, instead of coincidence detection, SPECT utilizes a technique known as collimation (Jaszczak R J. Boca Raton: CRC Press; (1991): 93-118). A collimator may be thought of as a lead block containing many tiny holes that is interposed between the subject and the radiation detector. Given knowledge of the orientation of a collimator's holes, the original path of a detected photon is linearly extrapolated and the image is reconstructed by computer-assisted tomography.

Magnetic Resonance Imaging, or MRI, produces a map of hydrogen distribution in the body. Hydrogen will align itself within a strong magnetic field like the needle of a compass. Once a patient's hydrogen atoms have been aligned in the magnet, pulses of very specific radio wave frequencies are used to knock them back out of alignment. The hydrogen atoms alternately absorb and emit radio wave energy, vibrating back and forth between their resting (magnetized) state and their agitated (radio pulse) state. In magnetic resonance studies, an object is put in a strong, externally imposed magnetic field ("main magnetic field"); the spin-axes of all the nuclei in the object line up with the field, with the north poles of the nuclei pointing in the "southward" direction of the field. This creates an average vector of magnetization of the object that points parallel to the magnetic field (the main magnetic field is conventionally referred to as pointing along the z-axis) (Horowitz, 1995).

A radiofrequency (RF) pulse is then broadcast toward the object in a line perpendicular to the magnetization vector. The RF pulse causes the axes of the nuclei to tilt with respect to the main magnetic field, thus causing the net magnetization vector to deviate from the main magnetic field by a certain angle. However, only the pulse will affect those nuclei that precess about their axes at the RF pulse frequency; in other words, the nuclei that "resonate" to that frequency will be affected (Horowitz, 1995). The net magnetization vector gradually returns to the state of being parallel with the external magnetic field, and the time that this takes is called the T2 relaxation time or "spin-spin relaxation time" after deactivation of the RF pulse. The amount by which the magnetization vector tilts away from the z-axis is controlled by the intensity and duration of the RF pulse (Horowitz, 1995).

The RF pulse also increases the angle of precession of the nuclei about their axes. This increase of precession angle affects the strength of the magnetization vector, since the nuclei's spin axes now deviate more from the z-axis than they did before the pulse, so that the standard deviation of this angle is high, although the mean of the angle is zero. Over time, as the standard deviation of the precession angle decreases, the strength of the net magnetization vector increases, since all the nuclei are gradually coming to point in the z-direction again. Over time, the angle of precession of the axes declines back to its resting state (wherein the average angle of precession is zero and the standard deviation of the angle of precession is low). The time that this takes is called "T1 relaxation time" or "spin-lattice relaxation time," and usually lasts between 200 and 2,000 msec (Horowitz, 1995).

As the nuclei relax, each gives out a characteristic pulse that changes over time, depending on the local microenvironment surrounding the proton. For example, hydrogen nuclei in fats have a different microenvironment than do those in water, and thus transmit different pulses. Due to these differences, in conjunction with the different water-to-fat ratios of different tissues, different tissues transmit different radio signals. These transmissions are used to form MRI images (Horowitz, 1995). MRI in biomedical science has two additional characteristics: 1) a 3-dimensional picture of the object is obtained, in addition to the chemical composition of the object; 2) the nuclei of hydrogen atoms are usually imaged (Horowitz, 1995).

MRI equipment records the duration, strength, and source location of the signals emitted by the atoms as they relax and translates the data into an image on a television monitor. The state of hydrogen in diseased tissue differs from healthy tissue of the same type, making MRI particularly good at identifying tumors and other lesions. In some cases, chemical agents such as gadolinium can be injected to improve the contrast between healthy and diseased tissue. A single MRI exposure produces a two-dimensional image of a slice through the entire target area. A series of these image slices closely spaced (usually less than half an inch) makes a virtual three-dimensional view of the area.

MRI can be used to create temporary features, called tags, within the body's tissues. Tagging utilizes special pulse sequences to spatially modulate the longitudinal magnetization of the subject. The tags, while visible over their (approximately) one-second lifetime, move with the motion of the heart. The pattern of tags can in turn be analyzed to understand the motion of the heart during its contraction and dilation. Usually tags are created at the beginning of a heartbeat and data to create images are acquired during systole and part of diastole. Typically, several heartbeats are required, over a brief breath-hold, to gather enough data to form a high-resolution MR image sequence of the tag motion. Heart motion is highly repeatable and many images taken from different orientations and at different times can be used to track material points in three dimensions, leading to detailed maps of the strain patterns within the myocardium.

Harmonic phase magnetic resonance imaging (HARP-MRI) is a promising new method that overcomes drawbacks of the other existing methods and makes it possible to use MR tagging possible in clinical applications (Osman, N. F. et al, (1999) *Magn. Reson. Med.* 42(6): 1048-60). The magnitude of a harmonic image is called a harmonic magnitude image, to distinguish it from the usual magnitude MR image. The other component of a harmonic image is called the harmonic phase image, or simply the HARP image. The spectrum of a harmonic image is spread over all spatial frequencies; but most of the spectral energy is concentrated around the spectral peaks. The HARP bandpass filter should be properly positioned in order to capture a certain fraction of the spectral energy (for example, 90%). The underlying motion of the heart will affect the size and position of this bandpass region as well. For example, a contraction of the heart causes an increase in spectral spreading, a tissue stretching orthogonal to the tag lines will cause a decrease in the magnitude of the central frequency of a spectral peak, and a tissue contraction will cause an increase in the central frequency.

In the heart, the mechanical strain is bound by the local contractility of the myocardial fibers. Thus, the expected size and position of a harmonic peak is limited. Other factors affect the computation of harmonic images. For example, the intensity of harmonic images fades in accordance with the tag fading, which reduces the SNR of the harmonic image. Also, interference from other harmonic peaks also produces artifacts. Fortunately, imaging parameters can be found that effectively balance these effects, yielding images that are capable of producing very accurate, reasonably high-resolution regional cardiac function measurements.

Harmonic images are very similar to tagged images, except that they appear to have tags that are sinusoidal patterns, and there are two of them—a cosine pattern and a sine pattern, corresponding to the real and imaginary parts of the harmonic image. When the heart moves, the underlying pattern of each harmonic image changes. For example, compression of the heart muscle causes the crests of the sinusoidal pattern to move closer together while stretching or elongation causes the crests to move farther apart. This means that there is a relationship between the frequency of a harmonic image and the compression and elongation—in other words, the strain—of the heart muscle.

HARP analysis methods exploit the following two properties: 1) for a given point, harmonic phase is constant with time and 2) the slope of the harmonic phase is linearly related to the underlying mechanical strain. Once imposed by the tagging process, the harmonic phase of a point in the tissue is constant throughout a motion or deformation. Motion tracking using HARP exploits this fact by using a phase-based optical flow formulation, which is referred to as CINE-HARP. A pair of tagged image sequences is used, usually with vertical and horizontal tags. These tag orientations provide sufficient information to track points in the plane. Out-of-plane motion is not tracked ordinarily, and therefore the tracking result must be interpreted as an apparent two-dimensional motion. This is consistent with the tag motion that is actually seen in two-dimensional images, so HARP tracking can be used to track tag lines, or anatomical features that is seen in the images.

Motion tracking uses an iterative algorithm that searches for the point in a second image that has the same two phase values as the point of interest in the first image. This process is repeated throughout the entire tag image sequence, yielding a pathline for the selected point. Points can be tracked both forward and backward in time as well. The tracking method can be used to measure Lagrangian strain by observing the change in distance between a pair of tracked points. Because of the special geometry of the heart and its function, it is common to measure the strain in the radial and circumferential directions. For this, a collection of points can be placed on a circular grid that fits the LV wall. The grid comprises three concentric circles representing the endocardium, midwall, and epicardium. Each circle has 16 points uniformly distributed on the circumference. All the points are tracked through the cardiac cycle and by measuring the change in distance between neighboring point on a circle provides a measure of circumferential strain. The distance between points neighboring on the radial direction produces the radial strain.

The second principle of HARP is the slope of the harmonic phase, which is related to strain. We refer to the measurement of strain made using this technique as "Single-shot HARP" because it does not require an image sequence. Instead, only one pair of harmonic phase images (vertical and horizontal) is required, both corresponding to a single time in a cardiac cycle. After calculating the slopes of these harmonic phase images at a given point, a two-dimensional strain tensor can be computed at that point. This is repeated over all points (pixels) in an image so that a strain tensor map is produced. Several measurements can be produced from these strain tensors: circumferential strain, radial strain, maximum and minimum strains, and the contraction angle. The contraction angle is the angle between the maximum contraction direction and the circumferential direction.

An echocardiogram is a test in which ultrasound is used to examine the heart. In addition to providing single-dimension images, known as M-mode echo that allows accurate measurement of the heart chambers, the echocardiogram also offers two-dimensional (2-D) Echo and is capable of displaying a cross-sectional "slice" of the beating heart, including the chambers, valves and the major blood vessels that exit from the left and right ventricle.

Doppler is a special part of the ultrasound examination that assesses blood flow (direction and velocity). In contrast, the M-mode and 2-D Echo evaluates the size, thickness and movement of heart structures (chambers, valves, etc.). During the Doppler examination, the ultrasound beams will evaluate the flow of blood as it makes it way though and out of the heart. This information is presented visually on the monitor (as color images or grayscale tracings and also as a series of audible signals with a swishing or pulsating sound).

Echocardiography provides important information about, among other structures and functions, the size of the chambers of the heart, including the dimension or volume of the cavity and the thickness of the walls. The appearance of the walls may also help identify certain types of heart disease that predominantly involve the heart muscle. Pumping function of the heart can also be assessed by echocardiography. One can tell if the pumping power of the heart is normal or reduced to a mild or severe degree. This measure is known as an ejection fraction or EF. A normal EF is around 55 to 65%. Numbers below 45% usually represent some decrease in the pumping strength of the heart, while numbers below 30 to 35% are representative of an important decrease. Echocardiography can also identify if the heart is pumping poorly due to a condition known as cardiomyopathy, or if one or more isolated areas have depressed movement due to prior heart attacks. Thus, echocardiography can assess the pumping ability of each chamber of the heart and also the movement of each visualized wall. The decreased movement, in turn, can be graded from mild to severe. In extreme cases, an area affected by a heart attack may have no movement (akinesia), or may even bulge in the opposite direction (dyskinesia). The latter is seen in patients with aneurysm of the left ventricle or LV.

Echocardiography identifies the structure, thickness and movement of each heart valve. It can help determine if the valve is normal, scarred from an infection or rheumatic fever, thickened, calcified, torn, etc. It can also assess the function of prosthetic or artificial heart valves. The additional use of Doppler helps to identify abnormal leakage across heart valves and determine their severity. Doppler is also very useful in diagnosing the presence and severity of valve stenosis or narrowing. Unlike echocardiography, Doppler follows the direction and velocity of blood flow rather than the movement of the valve leaflets or components. Thus, reversed blood direction is seen with leakages while increased forward velocity of flow with a characteristic pattern is noted with valve stenosis.

Echocardiography is used to diagnose mitral valve prolapse (MVP), while Doppler identifies whether it is associated with leakage or regurgitation of the mitral valve (MR). The presence of MR frequently prompts the use of antibiotics prior to any dental or non-sterile surgical procedure. Such action helps reduce the rare complication of valve infection.

The volume status of blood vessels can also be monitored by echocardiography. Low blood pressure can occur in the setting of poor heart function but may also be seen when patients have a reduced volume of circulating blood (as seen with dehydration, blood loss, use of diuretics or "water pill", etc.). In many cases, the diagnosis can be made on the basis of history, physical examination and blood tests. However, confusion may be caused when patients have a combination of problems. Echocardiography may help clarify the confusion. The inferior vena cava (the major vein that returns blood from the lower half of the body to the right atrium) is distended or increased in size in patients with heart failure and reduced in caliber when the blood volume is reduced. Echocardiography is useful in the diagnosis of fluid in the pericardium. It also determines when the problem is severe and potentially life threatening. Other diagnoses made by Doppler or echocardiography include congenital heart diseases, blood clots or tumors within the heart, active infection of the heart valves, abnormal elevation of pressure within the lungs, among others.

Myocardial perfusion reserve (MPR) quantifies the capacity of the circulatory response to a maximal increase in physiological demand (Siebert, J. E., et al, (2002) *Proc. Intl. Soc. Mag. Reson. Med. Vol.* 10). MPR indicates the net circulatory consequence from coronary lesions and other vascular states, regardless of their morphological appearance, including the compensation by collateral circulation. Current perfusion acquisition methods now provide adequate temporal and spatial resolution, SNR, and first-pass contrast enhancement ratio. MPR may be thought of as an equation wherein MPR=stress perfusion/rest perfusion, or:

$$MPR(x, y) = \frac{[S_{stress}(x, y)/k_{Lstress} \int BP_{stress}(t)dt]}{[S_{rest}(x, y)/k_{Lrest} \int BP_{rest}(t)dt]}$$

where $S_{stress}$=first-pass myocardial upslope in stress, $k_{Lstress/rest}$=lumped constants, $\int BP_{stress/rest}(t)$=integral of LV blood pool ROI for input function. The $k_{Lstress/rest}/k_{Lstress/rest}$ ratio is presumed=1.

MPR image calculation challenges: 1) cardiac phase shifts between stress and rest acquisitions, 2) stress-rest difference in diaphragm position, 3) cardiac phase jitter that introduces variability in LV edge features. Stress-rest mismatches of myocardial anatomy and the reliability of the input function normalization may pose the ultimate limitation of MPR imaging. Intensity correction of surface coil reception modulations is required to determine the input function normalization, for post-processing automation, to improve the qualitative assessment of cardiac perfusion images, movie loops, and time-intensity curves during interactive review of MPR quantitative images. Given the integrative and objective MPR images, interactive investigation of suspicious regions in the thresholded MPR image forms the core of perfusion exam interpretation. MPR imaging may provide quantitative, objective information to reduce variability in perfusion exam interpretation, and to document MR myocardial perfusion.

The present invention is additionally described by way of the following illustrative, non-limiting Examples, which provide a better understanding of the present invention and of its many advantages.

EXAMPLES

Example 1

Development of a Chronic Ischemia Model in Dogs

The study was designed as a case control study with a single experimental (n=5) and a single control (n=5) group of dogs. A chronic injury, for example, a myocardial infarct, was created in the same fashion in all animals. The experimental and control group differed only in the agent injected stem cells or cell-free media, respectively. The experimental timeline displayed in FIG. 1 outlines the protocol. The time dependent change in myocardial function following stem cell therapy was evaluated by direct comparison to the control group.

Twelve hours prior to the procedure, all solid food was removed from the animal's kennel. Each animal received antibiotic prophylaxis with Noxcell (3 mg/kg s.c.). Induction of anesthesia was accomplished through a combination of xylazine (500 mg) and Telazole™ (4 mg/kg). The animals were then endotracheally intubated and placed on a mechanical ventilator. Continued maintenance anesthesia (Isoflurane 1.5-2.0 vol %) antibiotic prophylaxis (Noxcell 3 mg/kg s.c.) and narcotic analgesia was provided throughout the course of the procedure.

Figure 2:
FIG. 2 depicts the LAD ischemia model. The instrument identifies ligature located on the LAD just distal to the first diagonal branch. An additional ligature was placed (denoted by arrow) to eliminate collateral circulation.

Following general anesthesia induction, the animal was positioned and antiseptically prepared for the completion of a left sided thorocotomy. The pericardium was incised, and the LAD and distal PDA identified and ligated. The pericardium was subsequently closed following this procedure. FIG. 2 depicts the LAD ischemia model, where the instrument identifies the ligature located on the LAD just distal to the first diagonal branch. Note an additional ligature was placed to eliminate collateral circulation.

Example 2

Isolation and Expansion of Canine MAPCs

Under general anesthesia, the legs and iliac crests of each animal was antiseptically prepared and draped. Percutaneous insertion of a Jamshidi bone marrow aspirate needle was advanced into the proximal femur of both hind legs in all animals. A total volume of approximately 30 ml of dog bone marrow was aspirated from each animal. The bone marrow harvest was carried out as per guidelines of the University of Minnesota Committee on the Use of Animal Subjects in Research. BM mononuclear cells (BMMNCs) were obtained by Ficoll-hypaque density gradient centrifugation (Sigma Chemical, St. Louis, Mo.).

Cells obtained from the mononuclear layer were plated in 15 ml of expansion medium supplemented with 10 ng/ml EGF and 10 ng/ml PDGF-BB in T150 flasks coated with 10 ng/ml fibronectin (FN). Expansion medium consisted of 60% low-glucose DMEM (Gibco-BRL), 40% MCDB-201 (Sigma), 1× insulin-transferrin-selenium (ITS), 1× linoleic acid-bovine serum album (LA-BSA), $10^{-9}$ M dexamethasone (Sigma), 100 U penicillin, and 1000 U streptomycin (Gibco). In addition, 2% fetal calf serum (FCS) was added. Once adherent cells were more than 50% confluent, they were detached with 0.25% trypsin-EDTA (Mediatech) and replated at a 1:4 dilution under the same culture conditions. Epidermal growth factor (EGF) was purchased from Sigma, and platelet-derived growth factor BB (PDGF-BB), vascular endothelial growth factor-B (VEGF-B), hepatocyte growth factor (HGF) and fibroblast growth factor (FGF) were purchased from R&D Systems (Minneapolis, Minn.). A representative sample from each of five doses administered to the experimental animals was evaluated for CD44, CD45, and DLA-1 antigens in a FACS Calibur Flow Cytometry System (Becton Dickinson, Mountain View, Calif.). Briefly, cells were detached and stained sequentially with primary antibodies followed by fluorescently labeled secondary antibodies. Four of the samples were determined to be 94% $CD45^-$ and 91% $DLA-1^-$ (dog leukocyte antigen-1). One of the samples was additionally determined to be 86% $CD44^-$.

Figures 3A, 3B:
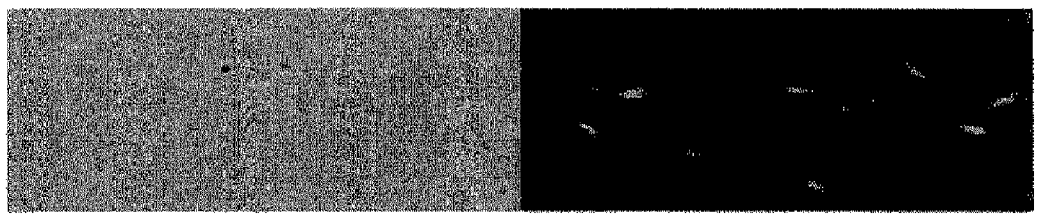
FIG. 3 depicts canine MAPCs prior to labeling (FIG. 3A) and after incorporation of GFP gene by retroviral transduction (FIG. 3B).
Figure 6:
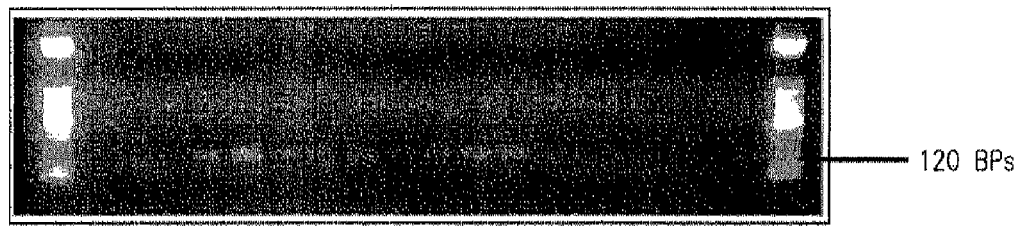
FIG. 6 depicts gel electrophesis demonstrating the eGFP product in multiple samples taken from three stem cell-treated animals.
Figure 7A:
FIG. 7 depicts delayed Gd-DPTA contrast enhanced cardiac MRI (FIG. 7A) raw image, raw image with contours added (FIG. 7B), and 3D reconstruction for infarct volume assessment (FIG. 7C).
Figure 7B:
Figure 7C:
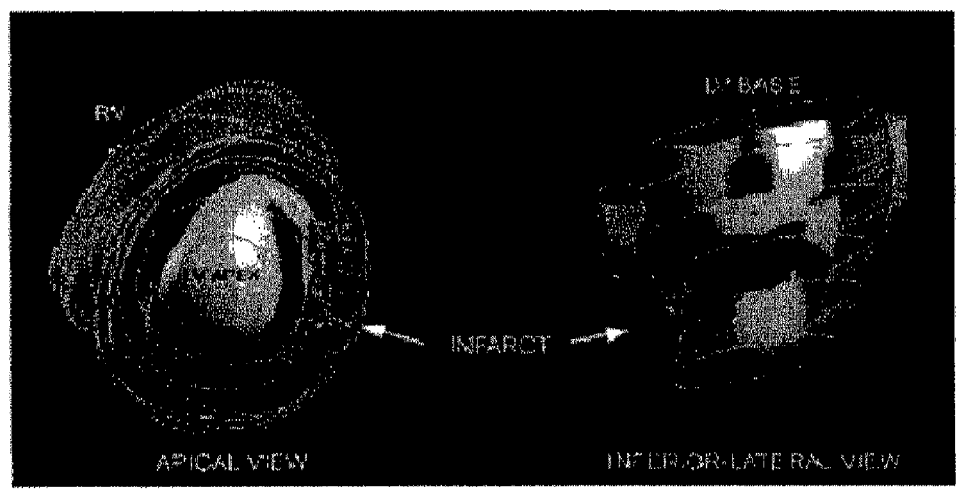
Figure 8A:
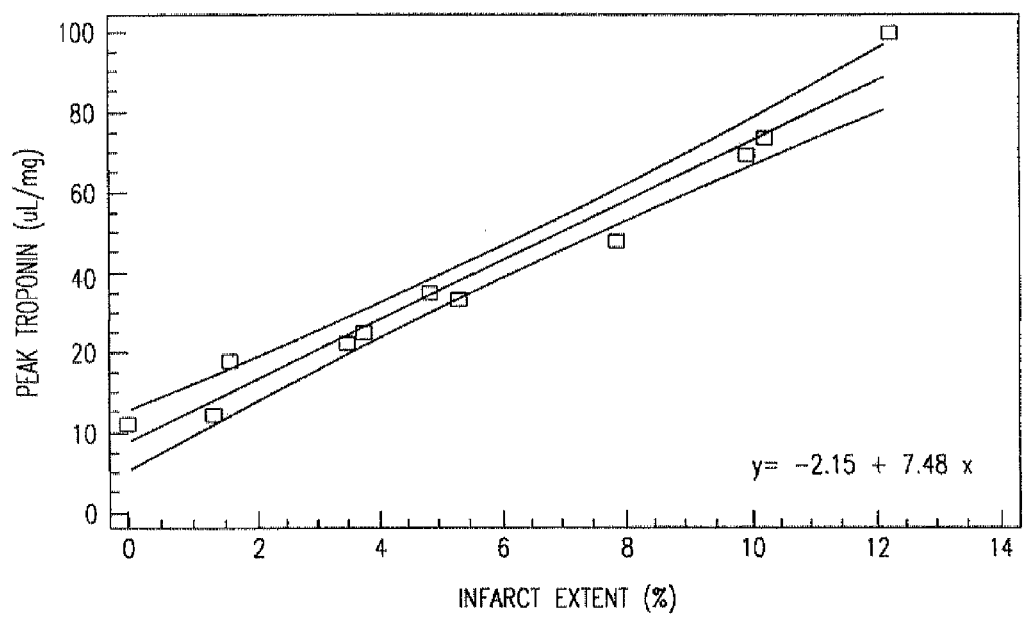
FIG. 8 depicts graphs showing linear regression curves plotted for infarct extent versus TnI concentration (FIG. 8A), infarct mass vs. TnI concentration (FIG. 8B), EF vs. TnI (FIG. 8C), and EF vs. infarct extent (FIG. 8D).
Figure 8B:
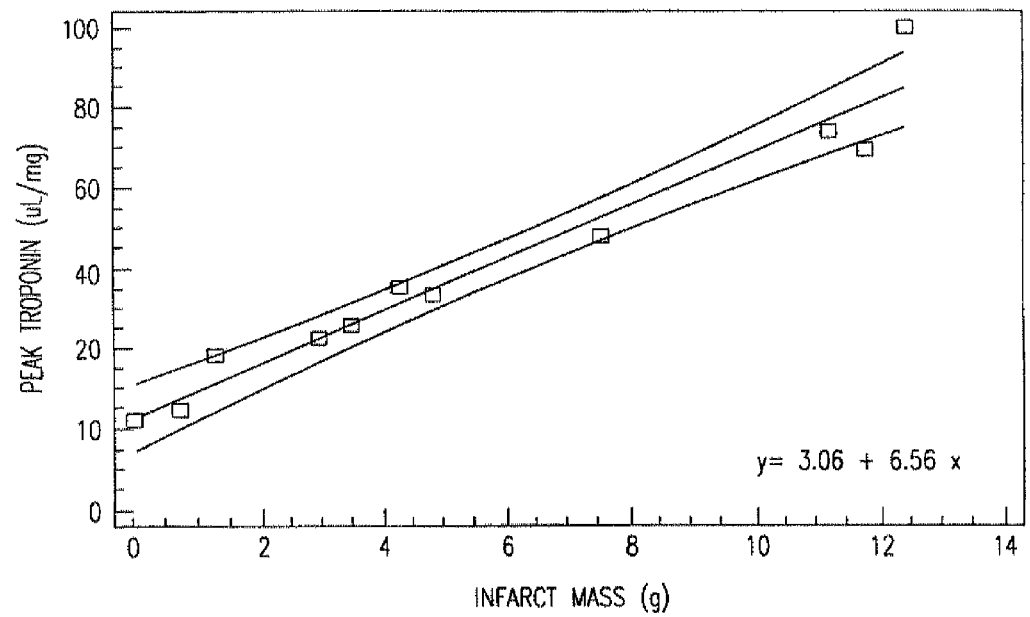
Figure 8C:
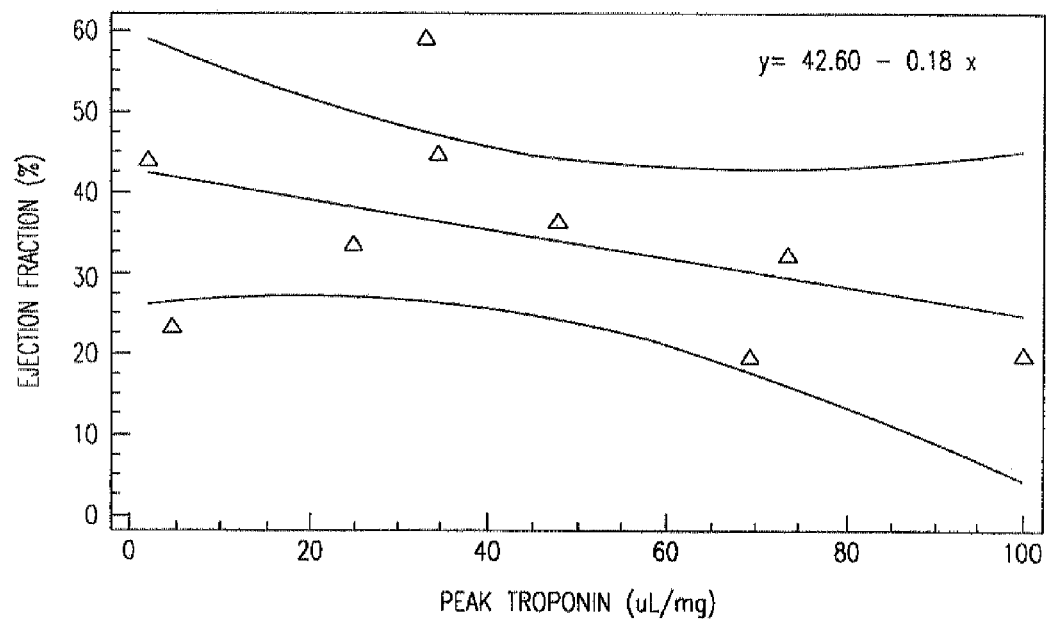
Figure 8D:
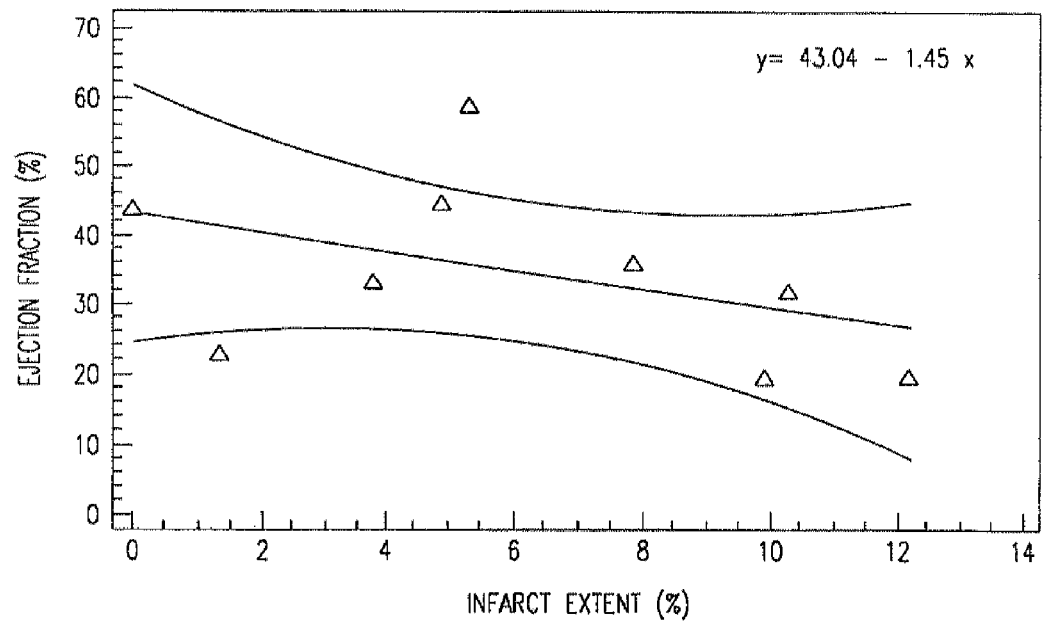

The cells were maintained at low density, approximately at $1500/cm^2$ to $2500/cm^2$ and passaged every 24-36 hours. The cells were expanded for 4 weeks, and then labeled by transduction with a MSCV retrovirus containing the Green Fluorescent Protein gene (GFP). The MAPCs were transduced twice for 12 hours with this retrovirus to ensure an adequate transduction. Once labeled with GFP, cells are detectable by fluorescent microscopy or by quantitative PCR directed at the GFP gene. FIG. 3 depicts canine MAPCs prior to labeled process in (A), and after incorporation of the GFP gene by retroviral transduction in (B).

Example 3

Differentiation of Canine MAPCs

Endothelium: To induce differentiation into endothelial cells, MAPCs obtained after 35 population doublings were replated at $3.0×10^4$ cells/$cm^2$ in fibronectin-coated chamber slides in 60% low glucose DMEM (Invitrogen) and 40% MCDB-201 (Sigma), supplemented with 1× insulin-transferrin-selenium, 1× linoleic acid-BSA, $10^{-8}$ M dexamethasone, $10^{-4}$ M ascorbic acid 2-phosphate (all from Sigma), 100 U penicillin and 1000 U streptomycin (Invitrogen), plus 10 ng/ml VEGF (R & D Systems). Cultures were maintained by media exchange every 4-5 days. In some instances, FCS (Hyclone Laboratories) was added. In some instances, cells were subcultured after day 9 at a 1:4 dilution under the same culture conditions and supplemented with 10% FCS for more than 20 population doublings.

Figure 12A:
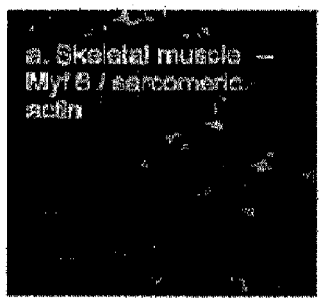
FIG. 12 depicts canine cells derived from the bone marrow showing progenitor cell characteristics with differentiation into mesodermal cell types. Skeletal muscle differentiation is shown at day 6 and stained for sarcomeric actin and Myf6 (overlay), and MyoD and sarcomeric actin (overlay) (FIG. 12A, B). Smooth muscle differentiation is shown by staining with smooth muscle myosin (FIG. 12C). Endothelial differentiation is shown by staining with antibodies against vWF (FIG. 12D) and shown to take up LDL (FIG. 12E) and staining in the nuclei is shown with TOPRO (FIG. 12F).
Figure 12B:
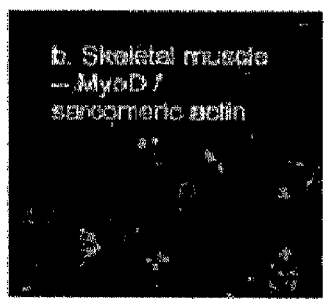
Figure 12C:
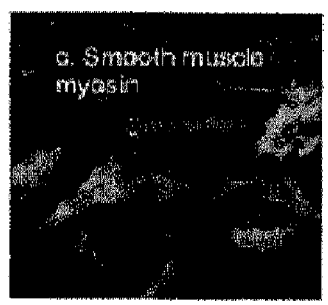
Figure 12D:
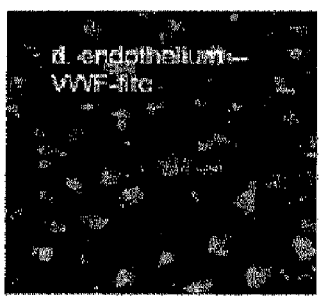
Figure 12E:
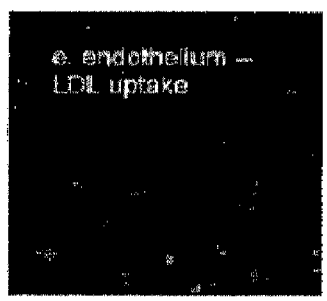
Figure 12F:
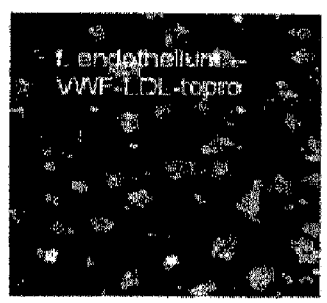

The cells attained a morphology characteristic of endothelial cells with cytoplasmic and morphological staining for vWF (FIG. 12d), which is also present at the RNA level (Table 3). The progeny of MAPCs that has been induced to differentiate with VEGF has functional characteristics of endothelial cells as well. For instance, we tested LDL uptake by incubating the MAPC-derived endothelial cells with DiI-Ac-LDL and cells were found to express vWF and to co-label with an LDL-specific dye (FIG. 12e). The DiI-Ac-LDL staining kit was purchased from Biomedical Technologies (Stoughton, MA). The assay was performed as per manufacturer's instructions.

Further, dog MAPCs were tested to determine if they could form vascular tubes when plated on Matrigel (Becton Dickinson, NJ). Extracellular matrix (Sigma) was added to a 24-well late at 0.5 ml/well and incubated for 3 hours at 37° C. MAPCs and MAPC-derived endothelial cells ($10^4$ per well) were added in 0.5 ml of serum-free medium containing 10 ng/ml VEGF and incubated at 37° C. As shown in FIG. 11, culture of MAPC-derived endothelial cells on extracellular matrix resulted in vascular tube formation within 6 hours.

Figure 15:
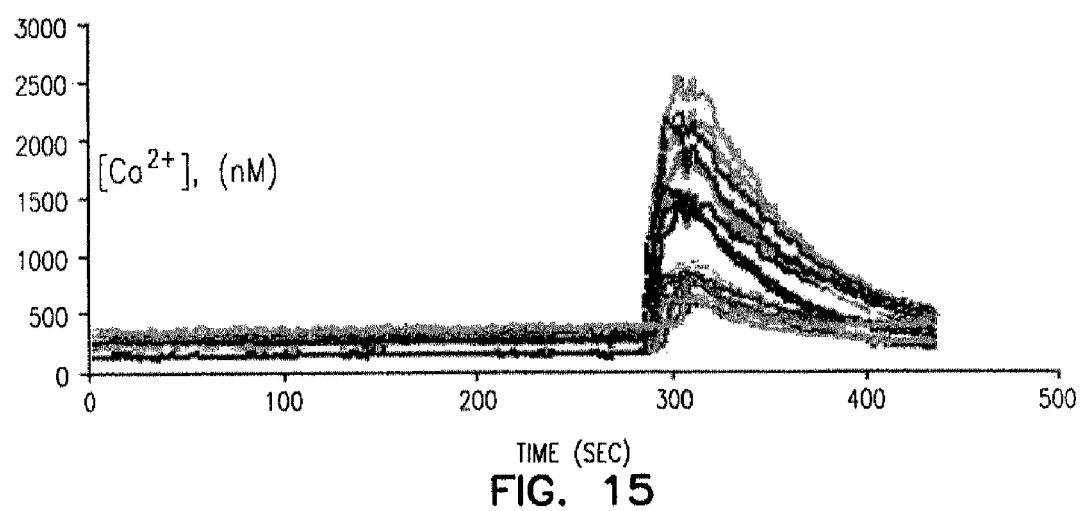
FIG. 15 depicts a graph of intracellular calcium flux in response to endothelin-1 (100 nM) using Fura-2AM real-time imaging in dog progenitor cell-derived smooth muscle differentiation following 12 weeks of differentiation. Each tracing represents an individual cell.
Figure 16A:
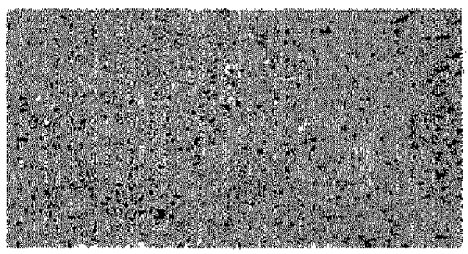
FIG. 16 depicts hematoxylin/eosin and Alcian Blue staining of a typical cartilage ball produced from canine MAPCs at high and low power magnification.
Figure 16B:
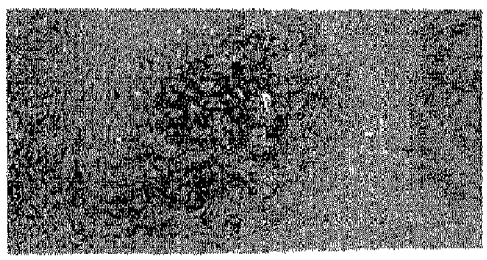
Figure 16C:
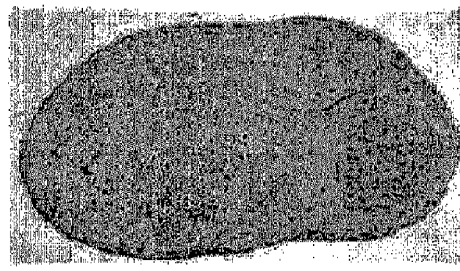
Figure 16D:
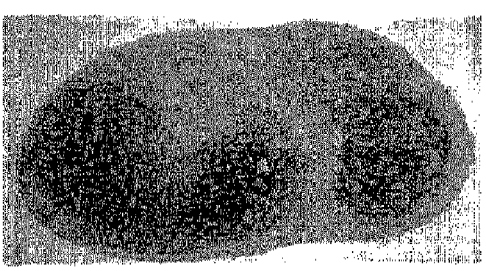

Smooth Muscle: To induce differentiation into smooth muscle, MAPCs obtained after 35 population doublings were replated at a density of $2.0 \times 10^4/cm^2$ in fibronectin-coated chamber slides in the serum-free, cytokine-free medium, containing all the rest of the ingredients present in medium described in Example 2. In addition, 100 ng/ml PDGF is added to induce smooth muscle specific differentiation. Cultures were maintained by media exchange every 4-5 days. Cells were subcultured after day 14 at a 1:4 dilution under the same culture conditions and supplemented with 5% FCS and 5 ng/ml PDGF for another 10 to 15 population doublings that reached up to 12 weeks in culture. As seen in FIG. 14, antibodies against smooth muscle myosin, smooth muscle actin, calponin, elastin, and caldesmin stained positive in the cytoplasm of the differentiated progeny. Staining was done at passage 4. Together, positive staining for the above antibodies argues for a smooth muscle phenotype of the differentiated dog MAPCs. Further, we attempted to functionally define the characteristics of the differentiated smooth muscle cells by evaluating for response to smooth muscle agonist endothelin-1. As shown in FIG. 15, prominent fluxes of intracellular calcium concentration were noted in many cells consistent with smooth muscle response to this agonist.

Real-time calcium uptake was monitored using the calcium sensitive dye Fura-2 AM. Briefly, cells were loaded with Fura-2 AM for 30 minutes and placed in a superfusion chamber on the stage of a fluorescence microscopy (Olympus IX-70) equipped with a digital camera (Photometrix Sensys) and a computer-controlled high speed filter wheel (Ludl Electronics). Data acquisition and analysis were performed with MetaFluor (Universal Images Inc.) software. Image pairs were acquired at 340 nm and 380 nm excitation wavelengths and 510 nm emission at intervals ranging from 2-10 seconds. Images were background-subtracted and ratioed (340/380) on a pixel-by-pixel basis. Average pixel values were then obtained from a region of each cell in the ratioed images and plotted versus time using GraphPad Prizm software. Cells were superfused with medium containing endothelin-1, the agonist, which was bath-applied using a four-way valve and gauged syringes.

Skeletal Muscle: To induce differentiation into skeletal muscle, MAPCs were replated at $3.0 \times 10^4$ in fibronectin-coated chamber slides in progenitor cell medium with 3 μm 5-azacytidine, 2% FCS, 10 ng/ml EGF, and 10 ng/ml PDGF-BB for the first 24 hours. Then, the medium was removed and cultured in regular progenitor cell medium for the next 14 days. Cultures were maintained by media exchange every 4-5 days. In some instances, cells were subcultured after day 14 at a 1:4 dilution under the same culture conditions for another 10 to 15 population doublings. Cultures were then evaluated by immunofluorescence to detect transcription factors and cytoskeletal proteins that are expressed during muscle development. After 6 days, cells stained positive for myf6 and myoD in the nuclei and for sarcomeric actin in the cytoplasm (FIGS. 12a and b), as well as dystrophin and desmin at the RNA level at day 14 (Table 3).

Figures 13A, 13B, 13C:
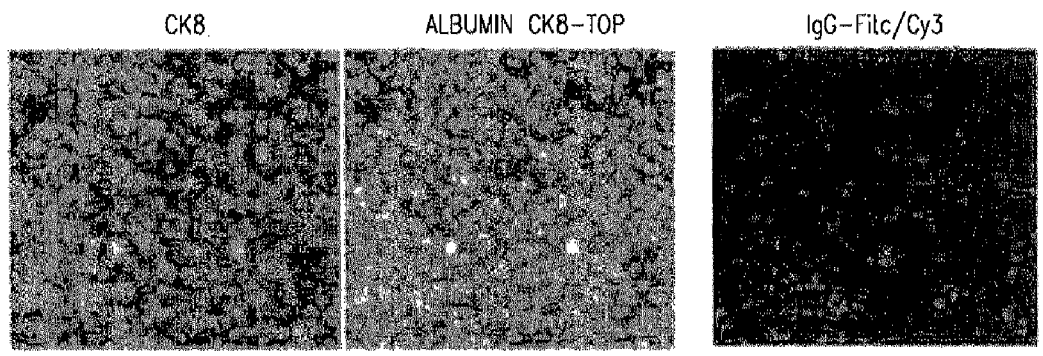
FIG. 13 depicts liver differentiation at day 28. Cytoplasmic staining for albumin and cytokeratin-8 are shown. IgG controls are shown on the right two slides.
Figures 13D, 13F, 13G:
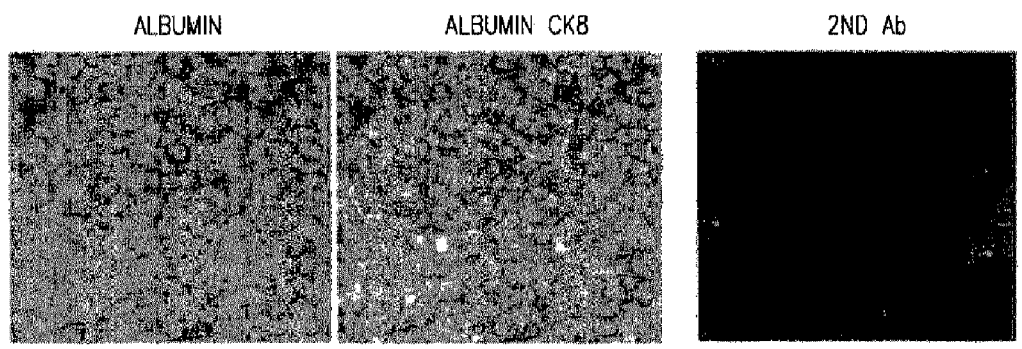
Figure 14A:
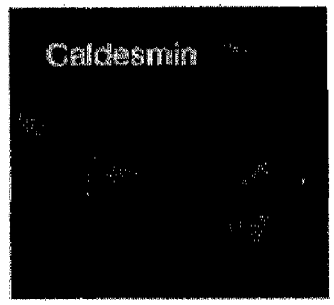
FIG. 14 depicts smooth muscle differentiation of canine MAPCs. Cells were stained at Day 14 for caldesmin, elastin, smooth muscle actin, calponin, and smooth muscle myosin. All antibodies are FITC-conjugated (green) show cytoplasmic staining only, and nuclei are labeled with TOPRO (blue).
Figure 14B:
Figure 14C:
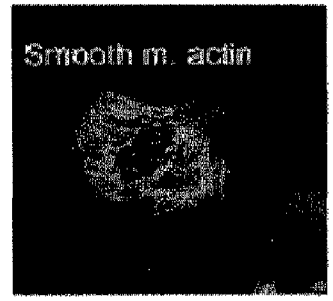
Figure 14D:
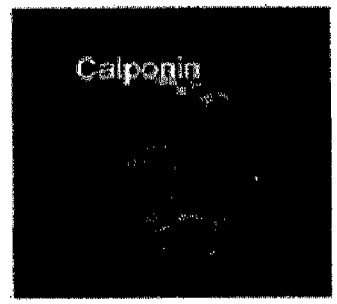
Figure 14E:
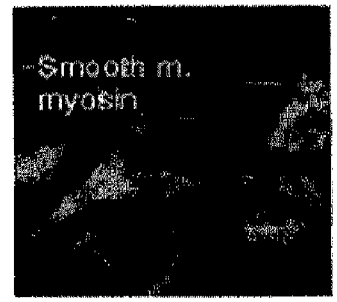

Hepatocyte differentiation: to induce differentiation into hepatocytes, MAPCs obtained after 35 population doublings were replated at $3.0 \times 10^4$ in Matrigel-coated chamber slides in 60% low glucose DMEM (Invitrogen) and 40% MCDB-201 (Sigma), supplemented with 1× insulin-transferrin-selenium, 1×LA-BSA, $10^{-8}$ M dexamethasone, $10^{-4}$ M ascorbic acid 2-phosphate (all from Sigma), 100 U penicillin and 1000 U streptomycin (Invitrogen), plus 20 ng/ml hepatocyte growth factor (HGF) and 10 ng/ml fibroblast growth factor 4 (FGF-4; both from R & D Systems) for 28 days. Media was changed every 4-5 days. Antibodies against albumin and cytokeratin-8 were found to stain positively and morphologically in the cytoplasm at day 28, as shown in FIG. 13 below. Albumin was also present at the RNA level (Table 3).

Cartilage: approximately $1 \times 10^6$ cells were resuspended in 1 ml of SF medium (comprising all components of MAPC expansion medium with exception of PDGF, EGF, and FCS)+ 10 ng/ml TGF-13 and 10 ng/ml IGF (insulin growth factor). Media was changed every 3-4 days for up to 14 days when cells formed a ball. The ball was fixed in 4% paraformaldehyde, which is 10% formalin. The tissue was paraffin-embedded and sectioned for hematoxylin and eosin, alcian Blue staining, type II and type X collagen staining.

MAPCs and differentiated MAPCs were characterized using immunofluorescence. For staining of cytoskeletal and nuclear proteins, cells were fixed with methanol at $-20°$ C. for 2 minutes and permeabilized with 0.1% Triton X-100 for 10 minutes. For other intracellular molecules, cells were fixed with 4% paraformaldehyde at 20° C. for 10 minutes. Blocking and diluent solution consisted of phosphate-buffered saline (PBS) 1% BSA, and 1% serum (Sigma) from species similar to the species in which the secondary antibody was raised. Slides were blocked for 30 minutes, incubated sequentially for 30 minutes each with antibodies against von Willebrand factor (vWF, 1:50 dilution), myf-6 (1:50), sarcomeric actin (1:50), smooth muscle actin, myoD (1:50), calponin, caldesmin, elastin, von Willebrand factor, albumin, cytokeratin-8, CD45, CD44, and DLA-1 antigens, and smooth muscle myosin (1:50). In between each step, slides were washed with PBS plus 0.3% BSA.

Total RNA was isolated from $5 \times 10^4$ MAPCs or MAPCs induced to differentiate to hepatocytes, endothelium and muscle. The mRNA was reverse transcribed and cDNA was amplified as follows: 40 cycles of a two-step PCR (95° C. for 15 seconds, 60° C. for 60 seconds) after initial denaturation (95° C. for 10 minutes) with 2 μl DNA solution, 1×TaqMan SYBR green universal mix PCR reaction buffer using a ABI PRISM 7700 (Perkin Elmer Applied Biosystems, Boston, Mass.). Primers used for amplification are listed in Table 1 (see below). Quantitative PCR data obtained from undifferentiated cells and differentiated cells is described in Table 2. The mRNA levels were normalized using GAPDH (dog) as housekeeping genes and compared with mRNA levels in freshly isolated tissue from the corresponding positive controls such as skeletal muscle, liver and lung (endothelium and smooth muscle).

TABLE 1

| Primer Name | Primer Sequence |
|---|---|
| Von Willebrand Factor | GGAGTCATCTCTGGATTCAAGC (SEQ ID NO: 1) |
| | GCTATAGGCAGACATCTCCCAC (SEQ ID NO: 2) |

TABLE 1-continued

| Primer Name | Primer Sequence |
|---|---|
| E-selectin | CTCAGGGTCATGAGTTCAAGC (SEQ ID NO: 3)<br>GTAGGCTCCACATCCAGCA (SEQ ID NO: 4) |
| Endothelin | CAGGCTTCTATGTGCTCCTCATGAT (SEQ ID NO: 5)<br>GTTGACCCAGATGATGTCAAGGTG (SEQ ID NO: 6) |
| α-fetoprotein | CAGGCTCAGGGTGTAGCACT (SEQ ID NO: 7)<br>GACGGCCTCAAGTTGCTCT (SEQ ID NO: 8) |
| Albumin | CCCAAGTGTCAACTCCAACTCT (SEQ ID NO: 9)<br>CAGCACAGGACATTCTCTGA (SEQ ID NO: 10) |
| HNF1-β | CTGTTCCCTTCCCAACAGG (SEQ ID NO: 11)<br>TTGATGACTGGCACGCTCT (SEQ ID NO: 12) |
| SAA | CTGGCCTGCCTGACAAGTA (SEQ ID NO: 13)<br>ATCTCAACGAGTGGGTGTCC (SEQ ID NO: 14) |
| Dystrophin | AGAGAACTCCATGAAGAGGCTG (SEQ ID NO: 15)<br>CTTGTCAATGGAAGAGAGGGAC (SEQ ID NO: 16) |
| Fast twitch-Myosin HC | GGGAAGACTGTGAACACCAAG (SEQ ID NO: 17)<br>GGTTGGCACTGATGATCTGA (SEQ ID NO: 18) |
| Slow twitch-Myosin HC | GACAGTCAACACCAAGAGGGTC (SEQ ID NO: 19)<br>GATGATCTGGTCCTCCAGAGTG (SEQ ID NO: 20) |
| Serca2A | GGTACACTGACAACGAACCAGA (SEQ ID NO: 21)<br>CATTAAGGGAGCAGCTATCACC (SEQ ID NO: 22) |
| ANP | CGCAGACCTGATGGATTTCAAG (SEQ ID NO: 23)<br>CGCTTCTTCATTCGGCTCACT (SEQ ID NO: 24) |
| Cardiac Myosin HC | GGTGCTCTACAACCTCAAGGAG (SEQ ID NO: 25)<br>GATGGAGAAGATGTGGGGC (SEQ ID NO: 26) |
| Muscarin B receptor | GAGAGGAGAAAGAGAGCTCCAA (SEQ ID NO: 27)<br>GGTGTTCTCATCCTGGGTTACTGGTGTTCTCAT<br>CCTGGGTTACT (SEQ ID NO: 29) |
| Phospholamban | ACCTGAGGAACAGAGGGAAA (SEQ ID NO: 30)<br>CTGAAGAAATCTCCCTGTTGG (SEQ ID NO: 31) |
| CTNNT2.F<br>cTNNT2.R | CGAACTGCAGACGCTGAT (SEQ ID NO: 32)<br>TCAGCTCCTCCTCCTCTTTC (SEQ ID NO: 33) |
| NF200 | CTTTCTCCCTTCCAGAAGGACT (SEQ ID NO: 34)<br>TGGATCTCCTCTGTCTGTTCCT (SEQ ID NO: 35) |
| S100 | CAGGAGGTCGTGGACAAG (SEQ ID NO: 36)<br>AGGTCAGCCCCGGAAAAG (SEQ ID NO: 37) |
| GFAP | CTTCCTGGAACAGCAGAACAAG (SEQ ID NO: 38)<br>GCTGTTGCCAGTGAGTTGGT (SEQ ID NO: 39) |
| Dendritic Receptor 2 | ACTGCACTCACCCTGAGGAC (SEQ ID NO: 40)<br>GCTGGACAGCATCTCCATCT (SEQ ID NO: 41) |
| Aggrecan | CTTCCATCCCAACTTCTCCA (SEQ ID NO: 42)<br>CTGGGAAAGCATAAGCATGT (SEQ ID NO: 43) |
| Desmin | CACCAGATCCAGTCCTACACCT (SEQ ID NO: 44)<br>GCAATGTTGTCCTGTAGCC (SEQ ID NO: 45) |
| GAPDH | GTGATGCTGGTGCTGAGTATG (SEQ ID NO: 46)<br>GTGATGGCATGGACGGTGG (SEQ ID NO: 47) |

TABLE 2

| Gene | Undifferentiated Cells (PD 50) | Endothelium | Skeletal Muscle | Hepatocyte |
|---|---|---|---|---|
| VWF | — | + | — | — |
| Dystrophin | — | — | + | — |
| Desmin | — | — | + | — |
| Albumin | — | — | — | + |
| GAPDH | + | + | + | + |

MAPCs and MAPCs induced to differentiate were also karyotyped by subculturing at 1:4 dilution for 12 hours before harvesting. Cells were collected with trypsin-EDTA and subjected to a 1.5-hour colcemid incubation followed by lysis with hypotonic KCl and fixation in acid/alcohol. Metaphases were analyzed by QFQ or GTG banding.

Example 4

Myocardial Stem Cell Therapy in a Canine Model of Ischemia

Stem Cell Injection: Following the baseline MRI imaging to establish infarct size and location, all animals underwent repeat thoracotomy under general anesthesia for myocardial injection. The injection of MAPC stem cells suspensions has been described in Reyes, M and C. M. Verfaillie (Ann. NY Acad. Sci. (2001) 938: p 231-3) and Institute of Laboratory Animal Resources, Guide for the Care and Use of Laboratory Animals. Injection can be completed as a single bolus perpendicular injection at the center of the infarction. Alternatively, a series of injections may be administered. In this instance a series of injections was administered, and each injection was completed by placing a 27 gauge needle centrally in the scar, directing the needle tangentially along the ventricular wall in a radial fashion 1.5 inches towards the peri-infarct region where the injection of stem cells begin. Injection was completed into the needle tract as the needle was withdrawn and prior to complete removal of the needle. A suture ligation of the entry point was used to seal the MAPCs in place and serve to mark the site of treatment. The injection of cells was completed in this fashion to allow for a gradient of nutrient exposure. Experimental canine animals were treated with 4 injections (mean=$12\times10^6$ stem cells/injection) totaling $48\times10^6$-labeled autologous undifferentiated MAPCs suspended in PBS. Similarly, the control animals were injected with an equal volume (1 cc/injection) of stem cell free media.

Clinical MRI Follow-Up: Animals were maintained under general anesthesia per protocol throughout the entirety of each imaging session. Cardiac MRI was completed on a Siemens Sonata scanner for each animal at 4 time points as described above. During each imaging session, images were acquired at rest and at stress (induced by continuous infusion of adenosine) states. Global function and perfusion were assessed by analysis of images acquired using Cine and True FISP image sequences (FIG. 4). Cine analysis (MASS software, Leiden, The Netherlands) endo- and epicardial borders of the LV were defined in end diastolic and end systolic frame in contiguous slices. Tagged data were analyzed using a custom written analysis package (HARP version 2.0), the technical aspects of HARP have been described elsewhere (see Detailed Description).

Harmonic phase imaging is based on the use of isolated peaks in the Fourier domain extracted with a band pass filter. The inverse Fourier transforms of one of these peaks is a complex image whose phase is linearly related to directional component of the true motion. The principle value of the phase was used to construct a HARP image, slopes of phase reflect the frequency of the tag patterns and phase images reflect motion of the heart. Two-dimensional myocardial strains were assessed off-line in 12 pie-shaped myocardial segments. To accurately correlate myocardial strain, Cine and delayed enhancement images from all data sets were cross registered with the anteroseptal intersection as anatomic landmark. Transmural strains were assessed between the reference (end-diastole) and the deformed state (end-systole) as fractional change in length in the circumferential (Ecc) and radial directions (Err) in the subendocardial, mid-wall and subepicardial layers. A negative value stands for compression of line segment between two material points (shortening or thinning), while positive values reflect strain (elongation stretching or thickening) depending on the direction of deformation (circumferential or radial, respectively).

Definition of Infarct, Adjacent, and Remote Regions: Delayed enhancement (DE) images were used to sort the myocardial tagging and Cine data during post processing as follows. Percent signal intensity increase on the delayed enhancement images (15-20 minutes after contrast injection) was computed as follows: $[(SI_d-SI_0)/SI_0]\times100\%$, where $SI_d$ is the signal intensity on the delayed enhancement images and $SI_0$ is the signal intensity before injection of contrast agent. The area of delayed enhancement was defined as the region where the signal intensity was greater than the mean+2SD of remote myocardium. This area was considered as being the infarcted region. All sectors within the delayed enhancement region were labeled as infarcted sectors. The sectors were bordered the infarcted sectors in either the circumferential or longitudinal direction were labeled as adjacent. The two sectors which contralateral opposite the infarcted sector on each slice were regarded as remote regions. The remote region was usually at post wall sector 6 and 7 in this myocardial infarction model.

Statistical Analysis: Mean values were expressed as mean±SE. Random effect model (PROC MIXED, SAS Institute Inc.) was used to estimate mean values and test for differences between treatment and control group at two and four months after infarct. Model included infarct size to control for unbalance between groups at baseline. Equal means were assumed at baseline for treatment and control groups. A two stage nested model was assumed: regions within subjects and repeated observations overtime. All tests were two tailed and a p-value of <0.05 was considered statistically significant.

Pathological Evaluation All animals having been randomized to the study groups reached the desired four-month follow-up endpoint and were terminated per University of Minnesota Research Annual Resources protocols. No evidence of tumor formation was noted by either MRI or gross pathological evaluation of the dog hearts treated using the autologous stem cells or control injections. Hearts were explanted, bisected in the short axis, and immediately flash frozen in OCT frozen sectioning material at liquid nitrogen temperatures. Whole heart sections were then completed (30 mm thickness). Sections were stored in an alternating fashion in either RNA later for Q-PCR or on clear tape (845 tape, 3M, Minneapolis, Minn.) for microscopic assessment.

Total Genomic DNA isolation and quantitative PCR: Genomic DNA was extracted from 25 mg of cardiac tissue (Qiagen DNeasy Tissue Kit). The DNA was amplified as follows: 40 cycles of a two-step PCR (95° C. for 15 seconds, 60° C. for 60 seconds) after initial denaturation (95° C. for 10 minutes) with 50 ng of DNA, 1×TaqMan SYBR green universal mix PCR reaction buffer using a ABIPRISM 7700 (Perkin Elmer Applied Biosystems, Boston, Mass.). Primers and probe used for amplification are listed below in Table 2. The DNA levels were normalized using GAPDH as housekeeping gene and compared with DNA levels in freshly isolated transgenic mouse cardiac tissue.

TABLE 3

| eGFP Primer Name | Primer Sequence |
| --- | --- |
| eGFP (67) | S: 5'-AGCAAAGACCCCAACGAGAA-3' (SEQ ID NO: 48)<br>A: 5'-GGCGGCGGTCACGAA-3' (SEQ ID NO: 49) |
| eGFP (67) Probe | VIC-CGCGATCACATGGTCCTGCTGG-TAMRA (SEQ ID NO: 50) |
| eGFP (95) | S: 5'-CGACGGCAACTACAAGAC-3' (SEQ ID NO: 51)<br>A: 5'-TAGTTGTACTCCAGCTTGTGC-3' (SEQ ID NO: 52) |

Model Demographics: Thirteen animals entered into the protocol. Three animals died before treatment randomization as a result of the establishment of large myocardial infarcts. Ten animals survived and were randomized into stem cell treated (n=5) and control (n=5) groups. Delayed contrast imaging was performed to measure the relative size of the ischemic zone for comparison with gross pathology (see FIG. 5). The extent of the infarctions was transmural in all animals. In addition, the size of the infarctions, as determined by delayed enhancement imaging completed one month after infarction and prior to treatment, was not significantly different between the two groups (8.56%±4.59% of the LV, versus 10.79%±2.78% in control group).

Stem Cell Engraftment by Quantitative PCR: Greater than 200 sections/heart have been analyzed by Q-PCR for 3 stem cell treated animals. Results from the remaining two treated animals are pending and are not reflected in the following report. Q-PCR results demonstrate engraftment at 6-18% engraftment of GFP labeled stem cells. Results were verified by gel electrophoresis, isolation of the identified band of 120 bps, and finally DNA sequencing. The identified product was positively identified as GFP, with a BLAST score of 99%.

MRI Assessment—Infarct Size: The use of serum troponin I (TnI) for the diagnosis of a myocardial infarction is common practice. However, the relationship between TnI levels and infarct size has only been poorly estimated. To better quantify this relationship for future use with the assessment of stem cell therapy, a precise correlation of TnI levels and infarct size using high resolution cardiac MRI was completed. Serum TnI was measured 12 to 14 hours following the ligation. Cardiac MRI imaging was completed 1 month later using a 1.5 Tesla Siemens Sonata system. Delayed enhancement images were acquired 15-20 minutes following the injection of extracellular contrast agent (Gd-DTPA) using a T1-weighted 3D FLASH sequence with inversion recovery preparation. Image analysis was performed with software (CARMA$^3$) for global function analysis and mapping of delayed enhancement and regional wall motion defects to a 3D model of the LV. Infarct extent (IE) was calculated as the ratio of the infarct volume and the total LV volume. Serum TnI (2.5 to 47.8 µg/L) and infarct extent (1.6 to 7.8%) was measured in the first 8 animals completed are reported at this time. A significant linear correlation between serum TnI and infarct extent as measured by cardiac MRI was determined (IE=0.1767 [TnI]−1.18; r=0.91; P=0.0046). Serum TnI levels correlate well with infarct size as measured by cardiac MRI in the dog model. Establishment of this correlation in humans will allow for the completion of risk stratification at the time of the initial diagnosis of the ischemic event. Such prognostic information will be useful in prediction of infarct size and may assist in determining ultimate stem cell dosing.

Figure 9:
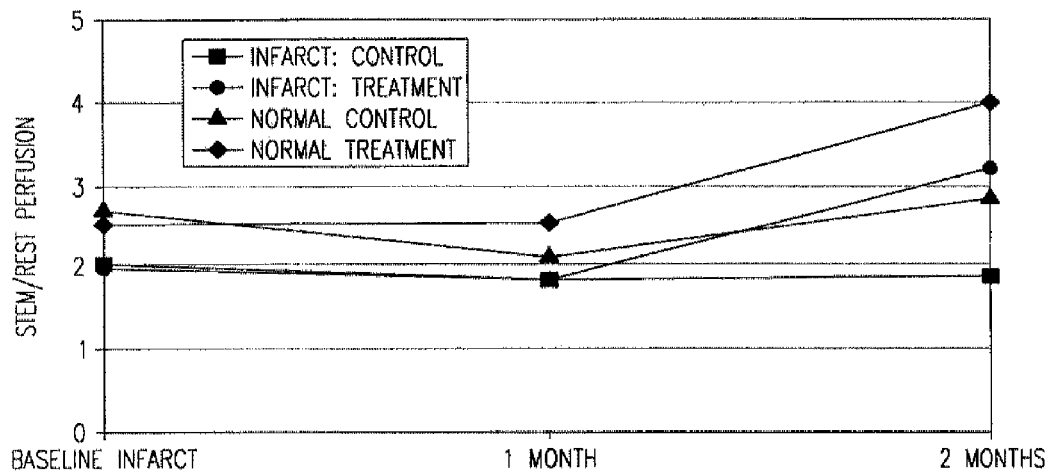
FIG. 9 depicts the mean perfusion reserve in a chronic dog infarct model. Results are reported for regions of normal (non-infarct) and target (ischemic) myocardial segments for stem cell-treated and control animals.

Perfusion: Myocardial perfusion reserve was determined by deconvolution of tissue residue SI curves from the LV input using a Fermi model for normal and target areas for four animals, where image quality was comparable. Segments within the target zone were compared to regions of normal myocardium (see FIG. 9). PR remained reduced in the infarct for sham operated animals. In contrast, PR doubled in the infarct for treated subjects, surpassing PR in normal segments of the sham operated animals.

Regional Myocardial Strains: Tagged MR imaging was performed in normal animals before MI and at baseline, with follow-up at 2 and 4 months following myocardial injection. Two-dimensional myocardial strains were assessed off-line in 12 pie-shaped myocardial segments. Both control and treated animals displayed profound reduction in regional myocardial strains at baseline. The most pronounced reduction of myocardial strain was found in the infarct region, and less strain reduction in the adjacent region, but strain reductions, although smaller, were also demonstrated in the remote regions. Of the stem cell treated group, 95 segments were used at each time point. Among them, there were 30 segments in the infarct regions, 35 in the adjacent regions, and 30 in the remote regions.

Figure 10:
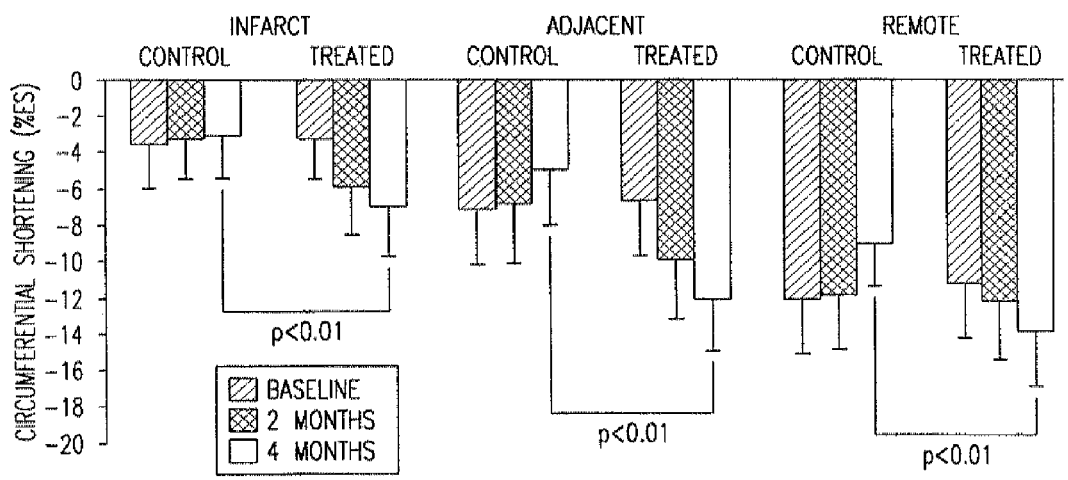
FIG. 10 depicts circumferential shortening as assessed by MRI strain imaging analysis using the HARP software package.
Figure 11A:
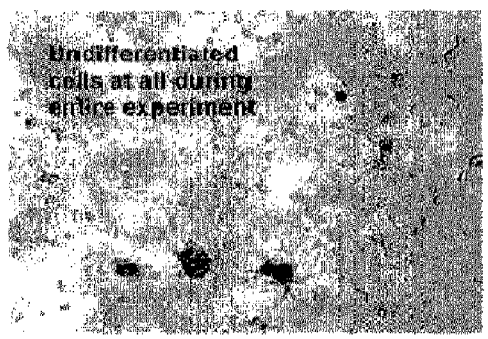
FIG. 11 depicts a vascular tube formation assay using undifferentiated MAPCs and endothelial differentiations at passage four.
Figure 11B:
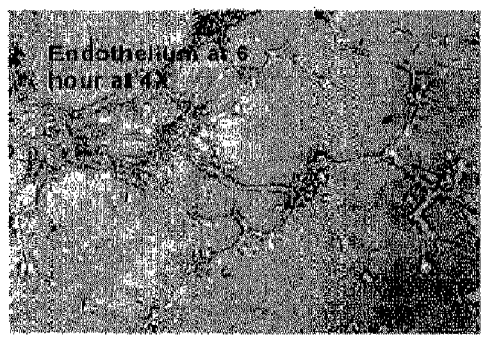
Figure 11C:
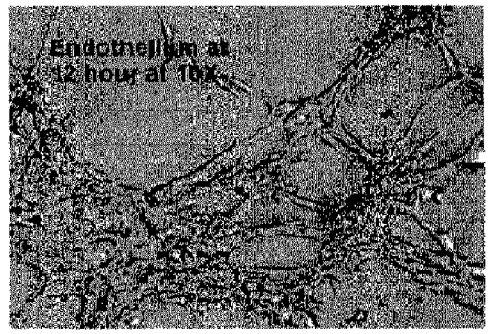
Figure 11D:
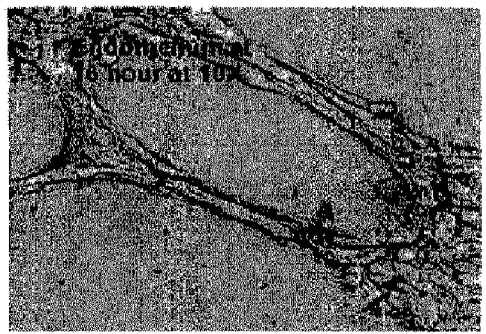

A total of 89 segments selected in control group at each time point were analyzed, 28 segments in the infarcted regions, 33 in the adjacent, and 28 in the remote regions. Changes in regional myocardial strain parameters Ecc and Err in stem cell-treated and control groups at all time point are summarized in FIG. 10. Myocardial strain parameters were obtained by averaging values of strains through wall (subendocardium, midwall and subepicardium) in each region in this figure. A sustained improvement of myocardial strains in all regions in the stem cell treated animals when compared with baseline and control animals at 2 and 4 months after transplantation. Circumferential shortening (Ecc) strain increased (p<0.05) as expected in the infarct and adjacent region at 2 and 4 months after stem cell implantation, but not in the cell free media injected group. At 4 months, the Ecc of the remote region had improved (p<0.05) in the stem cell implantation group, whereas no improvement was noted in the control group (FIG. 10). A significant (p<0.05) increase in the radial thickening (Err) was observed in adjacent regions at 2 and 4 months and only at 4 months in the infarct region after MAPC implantation relative to the control group. There was a trend of increase of Err in the remote region at 4 months after stem cell implantation, but not in the control group.

REFERENCES

Anversa, P., U.S. Patent Application Nos. 20020061587; 20020098167; and 20030054973

Asahara, T., Murohara, T., Sullivan, A., Silver, M., van der Zee, R., Li, T., Witzenbichler, B., Schatteman, G., and Isner, J. M.: "Isolation of putative progenitor endothelial cells for angiogenesis" (1997) Science 275(5302): 964-7.

Campion D R.: "The muscle satellite cell: a review" (1984) Int. Rev. Cytol. 87: 225-51.

Donovan, P. J. and Gearhart, J.: "The end of the beginning for pluripotent stem cells" (2001) *Nature* 414: 92-97.

Etzion, S., Battler, A., Barbash, I. M., Cagnano, E., Zarin, P., Granot, Y., Kedes, L. H., Kloner, R. A., and Leor, J.: "Influence of embryonic cardiomyocyte transplantation on the progression of heart failure in a rat model of extensive myocardial infarction" (2001) *J. Mol. Cell. Cardiol.* 33(7): 1321-30.

Grepin, C., Nemer, G., and Nemer, M.: "Enhanced cardiogenesis in embryonic stem cells overexpressing the GATA-4 transcription factor" (1997) Development 124(12): 2387-95.

Hoffman, E. J., Huang, S. C., Phelps, M. E., and Kuhl, D. E. "Quantitation in positron emission computed tomography: 4. Effect of accidental coincidences" 1981. *J. Comput. Assist. Tomogr.* 5: 391-400.

Hoffman, E. J., Phelps, M. E. "Positron emission tomography: principles and quantitation". In: Phelps, M., Mazziotta, J., Schelbert, H., eds. *Positron emission tomography and autoradiography: principles and applications for the brain and heart*. New York: Raven Press; 1986: 237-286.

Horowitz, A. L. *MRI Physics for Radiologists: A Visual Approach* ($3^{rd}$ Ed.) (1995) New York: Springer-Verlag Hughes S.: "Cardiac stem cells" (2002) *J. Pathol.* 197(4): 468-78.

Institute of Laboratory Animal Resources, t.N.R.C.a.t-.N.A.o.S., *Guide for the Care and Use of Laboratory Animals*. National Academy Press, 1996.

Jaszczak, R. J. "SPECT: state-of-the-art scanners and reconstruction strategies". In: Diksic, M., Reba, R. C., eds. *Radiopharmaceuticals and brain pathology studied with PET and SPECT* Boca Raton: CRC Press; 1991: 93-118.

Jiang, Y., Vaessen, B., Lenvik, T., Blackstad, M., Reyes, M. & Verfaillie, C. M.: "Multipotent progenitor cells can be isolated from postnatal murine bone marrow, muscle, and brain" (2002) *Exp Hematol.* 30(8): 896-904.

Jiang, Y., Jahagirdar, B., Reyes, M., Reinhardt, R. L., Schwartz, R. E., Chang, H.-C., Lenvik, T., Lund, T., Blackstad, M., Du, J., Aldrich, S., Lisberg, A., Kaushal, S., Largaespada, D. L. & Verfaillie, C. M.: "Pluripotency of mesenchymal stem cells derived from adult marrow" (2002) *Nature* 418: 41-9.

Kessler, P. D., and Byrne, B. J.: "Myoblast cell grafting into heart muscle: cellular biology and potential applications" (1999) *Annu. Rev. Physiol.* 61: 219-42.

Klug, M. G., Soonpaa, M. H., Koh, G. Y., and Field, L. J.: "Genetically selected cardiomyocytes from differentiating embronic stem cells form stable intracardiac grafts" (1996) *J. Clin. Invest.* 98(1): 216-24.

Kocher, A. A., Schuster, M. D., Szabolcs, M. J., Takuma, S., Burkhoff, D., Wang, J., Homma, S., Edwards, N. M., and Itescu, S.: "Neovascularization of ischemic myocardium by human bone-marrow-derived angioblasts prevents cardiomyocyte apoptosis, reduces remodeling and improves cardiac function." (2001) Nat. Med. 7(4): 430-6.

Krause, D. S., Theise, N. D., Collector, M. I., Henegariu, O., Hwang, S., Gardner, R., Neutzel, S. & Sharkis, S. I.: "Multi-organ, multi-lineage engraftment by a single bone marrow-derived stem cell" (2001) *Cell* 105: 369-77.

Lim, J. W., and Bodnar, A.: "Proteome analysis of conditioned medium from mouse embryonic fibroblast feeder layers which support the growth of human embryonic stem cells" (2002) *Proteomics* 2(9): 1187-1203.

Links, J. M. "Physics and instrumentation of positron emission tomography". In: Frost, J. J., Wagner, H. N., eds. *Quantitative imaging: neuroreceptors, neurotransmitters, and enzymes*. New York: Raven Press; 1990: 37-50.

Menasche P.: "Skeletal muscle satellite cell transplantation" (2003) *Cardiovasc. Res.* 58(2): 351-7.

Menasche, P., Hagege, A. A., Scorsin, M., Pouzet, B., Desnos, M., Duboc, D., Schwartz, K., Vilquin, J. T., and Marolleau, J. P.: "Myoblast transplantation for heart failure" (2001) *Lancet* 357(9252): 279-80

Orlic, D., Kajstura, J., Chimenti, S., Jakoniuk, I., Anderson, S. M., Li, B., Pickel, J., McKay, R., Nadal-Ginard, B., Bodine, D. M., Leri, A., and Anversa, P.: "Bone marrow cells regenerate infarcted myocardium" (2001) *Nature* 410 (6829): 701-5.

Orlic, D., Kajstura, J., Chimenti, S., Bodine, D. M., Leri, A., and Anversa, P.: "Transplanted adult bone marrow cells repair myocardial infarcts in mice" (2001) Ann. NY Acad. Sci. 938: 221-9; discussion 229-30.

Osman, N. F., Kerwin, W. S., McVeigh, E. R., and Prince, J. L.: "Cardiac motion tracking using CINE harmonic phase (HARP) magnetic resonance imaging" (1999) Magn. Reson. Med. 42(6): 1048-60.

Phelps, M. E., Hoffman, E. J., Huang, S. C., Ter-Pogossian, M. M. "Effect of positron range on spatial resolution". 1975. *J Nucl Med* 16: 649-652.

Reffelmann, T., and Kloner, R. A.: "Cellular cardiomyoplasty—cardiomyocytes, skeletal myoblasts, or stem cells for regenerating myocardium and treatment of heart failure?" (2003) *Cardiovasc Res.* 58(2): 358-68.

Reinecke, H., Poppa, V., and Murry, C. E.: "Skeletal muscle stem cells do not transdifferentiate into cardiomyocytes after cardiac grafting" (2002) *J. Mol. Cell. Cardiol.* 34(2): 241-9.

Reyes, M., and Verfaillie, C. M.: "Characterization of multipotent adult progenitor cells, a subpopulation of mesenchymal stem cells" (2001) Ann. NY Acad. Sci. 938: 231-3; discussion 233-5.

Sakai, T., Li, R. K., Weisel, R. D., Mickle, D. A., Jia, Z. Q., Tomita, S., Kim, E. J., and Yau, T. M.: "Fetal cell transplantation: a comparison of three cell types" (1999) *J. Thorac. Cardiovasc. Surg.* 118(4): 715-24.

Siebert, J. E., DeLano, M. C., Eisenberg, J. D., and Gupta, S. N.: "Myocardial Perfusion Reserve Imaging" (2002) *Proc. Intl. Soc. Mag. Reson. Med. Vol.* 10.

Sorenson, J. A., and Phelps, M. E. Physics in nuclear medicine, 2nd ed. Philadelphia: W.B. Saunders; 1987.

Takada, T., Suzuki, Y., Kondo, Y., Kadota, N., Kobayashi, K., Nito, S., Kimura, H., and Torii, R.: "Monkey embryonic stem cell lines expressing green fluorescent protein". (2002) Cell. Transplant. 11(7): 631-5.

Takahashi, T., Kalka, C., Masuda, H., Chen, D., Silver, M., Kearney, M., Magner, M., Isner, J. M., and Asahara, T.: "Ischemia- and cytokine-induced mobilization of bone marrow-derived endothelial progenitor cells for neovascularization" (1999) Nat Med. 5(4): 434-8.

Tomita, S., Li, R. K., Weisel, R. D., Mickle, D. A., Kim, E. J., Sakai, T., and Jia, Z. Q.: "Autologous transplantation of bone marrow cells improves damaged heart function" (1999) Circulation. 100(19 Suppl): II247-56.

Wang, J. S., Shum-Tim, D., Chedrawy, E., and Chiu, R. C.: "The coronary delivery of marrow stromal cells for myocardial regeneration: pathophysiologic and therapeutic implications" (2001) *J. Thorac. Cardiovasc. Surg.* 122(4): 699-705.

Wobus, A. M., Kaomei, G., Shan, J., Weilner, M. C., Rohwedel, J., Ji, G. J., Fleischmann, B., Katus, H. A., Hescheler, J., and Franz, W. M.: "Retinoic acid accelerates embryonic stem cell-derived cardiac differentiation and enhances development of ventricular cardiomyocytes" (1997) J Mol Cell Cardiol. 29(6): 1525-39.

The invention is further described by the following claims:

1. A method of providing striated muscle to a subject in need thereof, the method comprising administering to the subject, in amounts effective to provide new striated muscle, isolated human non-embryonic non-germ cells that do not express CD45 or glyA and express oct3/4, telomerase, rex-1, and rox-1, and are not transformed, wherein the subject has existing striated muscle, and wherein the isolated non-embryonic non-germ cells are expanded in cell culture medium prior to administration to the subject.

2. A method of increasing striated muscle mass, the method comprising contacting, in amounts effective to generate new striated muscle, isolated human non-embryonic non-germ cells that do not express CD45 or glyA and express oct3/4, telomerase, rex-1, and rox-1, and are not transformed, with existing striated muscle, and wherein the isolated non-embryonic non-germ cells are expanded in cell culture medium prior to administration to the subject.

3. A method for producing striated muscle cells in a subject, the method comprising administering to the subject, in amounts effective to produce striated muscle cells, isolated human non-embryonic non-germ cells that do not express CD45 or glyA and express oct3/4, telomerase, rex-1, and rox-1, and are not transformed, and wherein the isolated non-embryonic non-germ cells are expanded in cell culture medium prior to administration to the subject.

4. The method of claim 1, wherein existing striated muscle in the subject is damaged by disease.

5. The method of claim 4, wherein the disease is selected from the group consisting of congestive heart failure, coronary artery disease, myocardial infarction, myocardial ischemia, atherosclerosis, cardiomyopathy, idiopathic cardiomyopathy, cardiac arrhythmias, muscular dystrophy, muscle mass abnormalities, muscle degeneration, infective myocarditis, drug- and toxin-induced muscle abnormalities, hypersensitivity myocarditis, autoimmune endocarditis, and congenital heart disease.

6. The method of claim 1 or 2, wherein the new striated muscle is cardiac muscle.

7. The method of claim 1 or 2, wherein the new striated muscle is skeletal muscle.

8. The method of claim 1 or 3, wherein the isolated non-embryonic non-germ cells are administered using techniques selected from the group consisting of surgical intramyocardial injection, transendocardial injection, intracoronary injection, transvascular injection, intramuscular injection, intravenous injection and cardiac catheter administration.

9. The method of claim 3, wherein the striated muscle cells are cardiac muscle cells.

10. The method of claim 3, wherein the striated muscle cells are skeletal muscle cells.

11. The method of claim 1 or 3, wherein the subject is human.

12. The method of any one of claims 1-3, wherein the non-embryonic non-germ cells are isolated from bone marrow, muscle, brain, spinal cord, blood or skin.

13. The method of claim 1 or 3, wherein the non-embryonic non-germ cells are administered in the presence of cytokines, growth factors or a combination thereof.

14. The method of claim 1 or 3, wherein the administered non-embryonic non-germ cells are autologous cells.

15. The method of claim 1 or 3, wherein the administered non-embryonic non-germ cells are allogeneic cells.

16. The method of any of claims 1-3 wherein said isolated non-embryonic non-germ cells can differentiate into at least cell type of at least two of the mesodermal, endodermal, and ectodermal embryonic lineages.

17. The method of claim 16 wherein said non-embryonic non-germ cells can differentiate into at least one cell type of each of the endodermal, ectodermal and mesodermal lineages.

* * * * *